US010513434B2

(12) United States Patent
Seger et al.

(10) Patent No.: US 10,513,434 B2
(45) Date of Patent: Dec. 24, 2019

(54) NANOPIPETTE APPARATUS FOR MANIPULATING CELLS

(71) Applicant: The Regents of the University of California, Oakland, CA (US)

(72) Inventors: R. Adam Seger, Santa Cruz, CA (US); Paolo Actis, London (GB); Boaz Vilozny, Santa Cruz, CA (US); Nader Pourmand, Scotts Valley, CA (US)

(73) Assignee: The Regents of the University of California, Oakland, CA (US)

(*) Notice: Subject to any disclaimer, the term of this patent is extended or adjusted under 35 U.S.C. 154(b) by 13 days.

(21) Appl. No.: 15/463,860

(22) Filed: Mar. 20, 2017

(65) Prior Publication Data

US 2018/0002170 A1 Jan. 4, 2018

Related U.S. Application Data

(62) Division of application No. 13/406,269, filed on Feb. 27, 2012, now Pat. No. 9,598,281.

(Continued)

(51) Int. Cl.
*B82Y 15/00* (2011.01)
*B82Y 5/00* (2011.01)
(Continued)

(52) U.S. Cl.
CPC ............. *B82Y 5/00* (2013.01); *B01L 3/50273* (2013.01); *B01L 3/502715* (2013.01);
(Continued)

(58) Field of Classification Search
USPC .............. 73/863.32, 864.11, 864.24, 864.25; 422/501
See application file for complete search history.

(56) References Cited

U.S. PATENT DOCUMENTS 4,924,091 A 5/1990 Hansma et al.
5,567,588 A 10/1996 Gold et al.
(Continued)

FOREIGN PATENT DOCUMENTS

JP 2008271804 11/2008
WO WO 2004036202 4/2004
(Continued)

OTHER PUBLICATIONS

Matsuoka et al., Automatic Stop of a Microinjector Distinctively in the Cytosol or the Vacuole of Plant Single-cells, 2007, Electrochemistry, vol. 75, No. 7, pp. 513-517. (Year: 2007).*
(Continued)

*Primary Examiner* — Erik B Crawford
(74) *Attorney, Agent, or Firm* — Brian E. Davy; Bozicevic, Field & Francis LLP

(57) ABSTRACT

Disclosed herein are methods and systems for controlled ejection of desired material onto surfaces including in single cells using nanopipettes, as well as ejection onto and into cells. Some embodiments are directed to a method and system comprising nanopipettes combined with an xyz controller for depositing a user defined pattern on an arbitrary substrate for the purpose of controlled cell adhesion and growth. Alternate embodiments are directed to a method and system comprising nanopipettes combined with an xyz controller and electronic control of a voltage differential in a bore of the nanopipette electroosmotically injecting material into a cell in a high-throughput manner and with minimal damage to the cell. Yet other embodiments are directed to method and system comprising functionalized nanopipettes combined with scanning ion conductance microscopy for studying molecular interactions and detection of biomolecules inside a single living cell.

20 Claims, 9 Drawing Sheets

Related U.S. Application Data

(60) Provisional application No. 61/448,998, filed on Mar. 3, 2011.

(51) Int. Cl.
*B01L 3/00* (2006.01)
*G01Q 60/44* (2010.01)
*G01N 33/487* (2006.01)

(52) U.S. Cl.
CPC ........ *B82Y 15/00* (2013.01); *G01N 33/48728* (2013.01); *G01Q 60/44* (2013.01); *B01J 2219/00371* (2013.01); *B01L 2300/0645* (2013.01)

(56) References Cited

U.S. PATENT DOCUMENTS

| | | | | |
|---|---|---|---|---|
| 5,580,737 | A | 12/1996 | Polisky et al. | |
| 5,660,985 | A | 8/1997 | Pieken et al. | |
| 6,335,440 | B1 | 1/2002 | Lee et al. | |
| 7,592,188 | B2 * | 9/2009 | Hahn | C07D 403/06 106/31.15 |
| 7,655,791 | B2 | 2/2010 | Makarov et al. | |
| 7,708,871 | B2 | 5/2010 | Siwy et al. | |
| 2002/0076689 | A1 | 6/2002 | Farb et al. | |
| 2003/0152995 | A1 | 8/2003 | Hannah | |
| 2003/0219884 | A1 * | 11/2003 | Lison | G01N 33/5005 506/12 |
| 2004/0029101 | A1 * | 2/2004 | Orwar | C12N 15/89 435/4 |
| 2004/0182707 | A1 | 9/2004 | Jardemark et al. | |
| 2004/0241681 | A1 | 12/2004 | Korchev et al. | |
| 2005/0026181 | A1 | 2/2005 | Davis et al. | |
| 2005/0241940 | A1 | 11/2005 | Vasylyev et al. | |
| 2005/0260119 | A1 | 11/2005 | Sunkara et al. | |
| 2008/0132422 | A1 | 6/2008 | Bohlen et al. | |
| 2008/0202931 | A1 | 8/2008 | Petsev et al. | |
| 2008/0218184 | A1 | 9/2008 | White et al. | |
| 2009/0136958 | A1 | 5/2009 | Gershow et al. | |
| 2009/0318363 | A1 | 12/2009 | Rigal et al. | |
| 2010/0072080 | A1 | 3/2010 | Karhanek et al. | |
| 2010/0248977 | A1 * | 9/2010 | Johnston | C07K 7/08 506/9 |
| 2010/0285210 | A1 | 11/2010 | Choi | |
| 2011/0003326 | A1 * | 1/2011 | Graf | C12M 23/50 435/29 |
| 2011/0131690 | A1 * | 6/2011 | Novak | B82Y 35/00 850/43 |
| 2013/0017553 | A1 | 1/2013 | Orwar et al. | |

FOREIGN PATENT DOCUMENTS

| | | |
|---|---|---|
| WO | WO 2006000064 | 1/2006 |
| WO | WO 2008075842 | 6/2008 |

OTHER PUBLICATIONS

Actis et al. (2010) “Ultrasensitive mycotoxin detection by STING sensors,” Biosensors and Bioelectronics, 6(2):333-337.

Bruckbauer et al. (2003) “Multicomponent submicron features of biomolecules created by voltage controlled deposition from a nanopipet”, J Am Chem Soc., 125:9834-9839.

Choi et al. (2006) “Biosensing with conically shaped nanopores and nanotubes”, Phys. Chem. Chem. Phys., 8:4876-4988.

Hideaki et al. Machine Translated Copy of JP 2008-271804, 19 pages.

International Search Report and Written Opinion, PCT/US2012/026781, dated Feb. 27, 2013.

Laforge et al. (2007) “Electrochemical attosyringe”, PNAS, 104(29):11895-11900.

Li et al. (2009) “Development of boronic acid grafted random copolymer sensing fluid for continuous glucose monitoring”, NIH Public Access Author Manuscript, from Biomacromoecules, 10(1):113-118, doi:10.1021/bm8009768.

Mulla et al. (2004) “3-Methoxycarbonyl-5-nitrophenyl boronic acid: high affinity dial recognition at neutral pH”, Bioorganic & Medicinal Chemistry Letters, 14:25-27.

Office Action, JP Patent Application No. 2013-556777, dated Dec. 1, 2015, 8 pp.

Supplementary Partial European Search Report, EP20120815407, dated Nov. 27, 2014.

Rodolf et al. (2005) “Two-component graded deposition of biomolecules with a double-barreled nanopipette”, Angewandte Chem. Int. Ed., 44:6854-6859.

Rodolf et al. (2006) “Nanoscale pipetting for controlled chemistry in small arrayed water droplets using a double-barrel pipet”, Nano Letters, 6(2):252-257.

Umehara et al. (2009) “Label-free biosensing with functionalized nanopipette probes”, PNAS, 106(12):4611-4616.

YING et al. (2005) “The scanned nanopipette: a new tool for high resolution bioimaging and controlled deposition of biomolecules”, Phys Chem Chem Phys., 7:2859-2866.

Ying (2009) “Applications of nanopipettes in bionanotechnology” Biochem. Soc. Trans. 37:702-706.

* cited by examiner

NANOPIPETTE APPARATUS FOR MANIPULATING CELLS

CROSS-REFERENCE TO RELATED APPLICATIONS

This application claims priority from U.S. Provisional Patent Application No. 61/448,998 filed on Mar. 3, 2011, and is a divisional application of U.S. application Ser. No. 13/406,269, filed on Feb. 27, 2012, which are hereby incorporated by reference in their entirety.

STATEMENT OF GOVERNMENTAL SUPPORT

This invention was made with Government support under Contract Number NCC9-165 and NNX08BA47A awarded by the National Aeronautics and Space Administration (NASA), Contract Number P01-HG000205 awarded by the National Institutes of Health, Contract Number NNX09AQ44A awarded by NASA and under Contract Number U54CA143803 awarded by the National Cancer Institute. The Government has certain rights in the invention.

REFERENCE TO SEQUENCE LISTING, COMPUTER PROGRAM, OR COMPACT DISK

None.

BACKGROUND OF THE INVENTION

Field of the Invention

The present invention relates to the field of nanodevices and nanosensors for single cell injection, patterning and detection of biomolecules.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Nanopipette technology has been shown to be a capable platform for many applications. Actis et al., (including two of the present inventors) developed a sensing platform, named STING ("Signal Transduction by Ion Nano Gating"), where the very tip of a quartz nanopipette is functionalized with chemical or biological receptors (Actis, P., O. Jejelowo, and N. Pourmand, *Ultrasensitive mycotoxin detection by STING sensors*. Biosensors & Bioelectronics, 2010. 26(2): p. 333-337). The nanometer scale opening at the tip creates a region that is sensitive to analyte binding with the attached receptors. Additionally, Rodolfa, et al., have shown that nanopipettes can be used for controlled deposition onto functionalized surfaces (Rodolfa, K. T., et al., *Two-component graded deposition of biomolecules with a double-barreled nanopipette*. Angewandte Chemie-International Edition, 2005. 44(42): p. 6854-6859). Further work has demonstrated deposition of material onto a surface in an inorganic solvent (Rodolfa, K. T., et al., *Nanoscale pipetting for controlled chemistry in small arrayed water droplets using a double-barrel pipet*. Nano Letters, 2006. 6(2): p. 6). Individual molecules were delivered to cells' plasma membranes using nanopipettes (Bruckbauer, A., et al., *Nanopipette delivery of individual molecules to cellular compartments for single-molecule fluorescence tracking*. Biophysical Journal, 2007. 93: p. 3120-3131).

Laforge et al. developed an electrochemical attosyringe, based on a nanopipette that delivers liquid by applying a voltage across the liquid/liquid interface formed at the nanopipette opening (Laforge, F. O., et al., *Electrochemical attosyringe*. Proceedings of the National Academy of Sciences of the United States of America, 2007. 104(29): p. 11895-11900). The resulting force is sufficiently strong to induce the flow of liquid into/out of the pipette. They have successfully used this effect to deliver femtoliters of aqueous solution into mammalian cells in culture. Carbon nanopipettes have shown efficacy in cell injection as well. Pressure driven injection of fluorescent dyes into oral squamous carcinoma cells was demonstrated by Schrlau, et.al. (*Carbon nanopipettes for cell probes and intracellular injection*. Nanotechnology, 2008: p. 015101-1-4).

Cell Patterning

Controlling cell attachment and growth has emerged as an important topic in biological disciplines from neuroscience to stem cell research (James, C. D., et al., *Aligned microcontact printing of micrometer-scale poly-L-lysine structures for controlled growth of cultured neurons on planar microelectrode arrays*. Ieee Transactions on Biomedical Engineering, 2000. 47(1): p. 17-21; Welle, A., et al., *Photochemically patterned polymer surfaces for controlled PC-12 adhesion and neurite guidance*. Journal of Neuroscience Methods, 2005. 142(2): p. 243-250). By controlling where and how cells grow and mature, specific characteristics can be induced during cell growth. For instance, it has been shown by Oliva, et.al. (*Patterning axonal guidance molecules using a novel strategy for microcontact printing*. Neurochemical Research, 2003. 28(11): p. 1639-1648), that neuron differentiation can be controlled by chemical cues, allowing the direction of axon growth to be predetermined and customized for specific experiments. Similarly, inkjet printing has been shown to be capable of controlling neural stem cell differentiation (Ilkhanizadeh, S., et al., *Inkjet printing of macromolecules on hydrogels to steer neural stem cell differentiation*. Biomaterials, 2007. 28(27): p. 3936-3943).

Cell patterning has been investigated using a multitude of methods. By leveraging the advancements made in semiconductor fabrication technology patterns with feature sizes small enough to guide single cells has been made possible. The most widely used cell patterning technique is microcontact printing (μCP), whereby a master mold is fabricated using traditional photolithography, and an elastomeric stamp is created from the master. The stamp can then be inked with biomolecules and the pattern can be applied to an arbitrary substrate (Wilbur, J. L., et al., *Microfabrication by microcontact printing of self-assembled monolayers*. Advanced Materials, 1994. 6(7-8): p. 600-604). This method has seen wide success in controlling cell growth, particularly in the arena of controlled neural growth (Park, T. H. and M. L. Shuler, *Integration of cell culture and microfabrication technology*. Biotechnology Progress, 2003. 19(2): p. 243-253). Photolithography itself can be used for patterning as well. By exposing a substrate to radiation through a mask, surface chemistry can be modified, thus allowing specific attachment molecules to be placed in the appropriate regions (Welle, A., et al., *Photo-chemically patterned polymer surfaces for controlled PC-12 adhesion and neurite guidance*. Journal of Neuroscience Methods, 2005. 142(2): p. 243-250). Topographic cues have been shown to control cell growth as well. By changing the surface roughness that cells interface with cells adhesion can be controlled. The combination of chemical and topographical attachment cues has even been demonstrated as leading to improved cell differentiation (for example, Stenger, D. A., et al., *Microlithographic determination of axonal/dendritic polarity in cultured hippocampal neurons*. Journal of Neuroscience Methods, 1998. 82(2): p. 167-173). The drawback to these methods is that once the pattern has been designed and fabricated it cannot be changed without designing a new mask and restarting the entire process from scratch. Some methods have been developed for patterning that do not rely on standard semiconductor fabrication technology, and therefore are not limited by the fabrication process. Gustaysson, et al., (*Neurite guidance on protein micropatterns generated by a piezoelectric microdispenser*. Biomaterials, 2007. 28(6): p. 1141-1151) demonstrated a piezo actuated microdispenser capable of depositing 100 pL droplets with a precision of 6-8 μm. Dip pen and fountain pen lithography allows spot sizes as small as 40 nm to be deposited in an arbitrary user defined pattern as shown by Schmidt, R. C. and K. E. Healy (*Controlling biological interfaces on the nanometer length scale*) in Journal of Biomedical Materials Research Part A, 2009. 90A(4): p. 1252-1261. However this technique is limited to deposition of only a single pattern at a given time.

By using quartz nanopipette technology described below, the pattern deposited on a substrate is computer controlled and can thus be modified at any time by the user, and is capable of easily depositing multiple patterns that are registered relative to each other. The pattern can be used to accomplish cell attachment, as shown in FIG. 2, to a substrate 216, where a cell 212 is attached to a point on the substrate where an adhesion material has been deposited.

Cell Injection

Methods for cell injection have historically used a pulled glass micropipette. Traditional micropipettes suffer from several drawbacks including large size relative to typical cells, low cell viability, lack of feedback and the requirement of a skilled operator (Pillarisetti, A., et al., *Evaluating the effect of force feedback in cell injection*. Ieee Transactions on Automation Science and Engineering, 2007. 4(3): p. 322-331; Stephens, D. J. and R. Pepperkok, *The many ways to cross the plasma membrane*. Proceedings of the National Academy of Sciences of the United States of America, 2001. 98(8): p. 4295-4298).

A multitude of other methods for cell injection have been developed to alleviate these drawbacks. Methods such as electroporation, and the use of the pore forming toxin streptolysin-O (SL-O) have been developed for passive transfer of material into the cell (Wang, M. Y., et al., *Single-cell electroporation*. Analytical and Bioanalytical Chemistry, 2010. 397(8): p. 3235-3248; Knight, D. E. and M. C. Scrutton, *Gaining access to the cytosol—the technique and some applications of electropermeabilization*. Biochemical Journal, 1986. 234(3): p. 497-506; Giles, R. V., et al., *Selecting optimal oligonucleotide composition for maximal antisense effect following streptolysin O-mediated delivery into human leukaemia cells*. Nucleic Acids Research, 1998. 26(7): p. 1567-1575). Electroporation has been demonstrated to induce transient permeability in the cell membrane by application of high voltage, after which material can diffuse in. Cells have shown the ability to heal SL-O lesions under certain circumstances. In both cases, stress is introduced to the cell, and in the case SL-O lesions uptake is limited to ~100 kDa.

Direct methods of cell injection have been demonstrated using other unrelated nanofabricated structures. A nanoneedle, fabricated on AFM tips and coated with DNA was inserted into a single cell. Injection was accomplished by diffusion of DNA from the nanoneedle (Sung-Woong, H., et al., *High-efficiency DNA injection into a single human mesenchymal stem cell using a nanoneedle and atomic force microscopy*. Nanomedicine: Nanotechnology, Biology and Medicine, 2008: p. 215-25). Similarly, quantum dots were delivered by cleavage of disulfide bonds linking the dots to a nanoneedle within a cell (Chen, X., et al., *A cell nanoinjector based on carbon nanotubes*. Proceedings of the National Academy of Sciences of the United States of America, 2007. 104(20): p. 8218-8222).

Single Cell In Vivo Detection of Intracellular Molecular Species

Several methods allowing intracellular recording have been developed. Kopelman and coworkers (Tan, W., et al., *Submicrometer intracellular chemical optical fiber sensors*. Science 258, 778-781, doi:10.1126/science.1439785, 1992; Barker, S. L. R., et al., *Cellular Applications of a Sensitive and Selective Fiber-Optic Nitric Oxide Biosensor Based on a Dye-Labeled Heme Domain of Soluble Guanylate Cyclase*. Analytical Chemistry 71, 2071-2075, doi:10.1021/ac9901081, 1999) pioneered the application of chemical modified tapered optical fiber for the extracellular monitoring of pH and nitric oxide. Vo-Dihn and coworkers reported the analytical application of antibody modified optical fiber for measurement of a fluorescent analyte in a single cell (Vo-Dinh, T., et al., *Antibody-based nanoprobe for measurement of a fluorescent analyte in a single cell*. Nat Biotech 18: 764-767, 2000). One of the advantages of employing tapered optical fiber relies on high spatial resolution achievable using near field scanning optical microscopy. Sensors must be carefully manipulated under a microscope to avoid damage to cells. In addition to these physical constraints, the selective detection of biomolecules by affinity methods is itself challenging due to the many interfering species inside the cytoplasm. More recently an optical fiber nanobiosensor was constructed to detect a cancer biomarker into a single cell through an enzymatic sandwich immunoassay (Zheng, X. T. & Li, C. M. *Single living cell detection of telomerase over-expression for cancer detection by an optical fiber nanobiosensor*. Biosensors and Bioelectronics 25: 1548-1552, 2010). Electrical detection methods are known to be more suitable than other methods due to improved durability, sensitivity, rapid response, and integration with other device components. Even so, electrical-based sensors for intracellular measurements face many challenges. Microelectrodes, are usually large enough to damage typical mammalian cells (5 to 10 μm), and procedures are often limited to measurements in oocytes and embryos, which are at least ten times larger. Recently, microelectrodes protruding inside cells were employed to measure sub-threshold synaptic potentials by Hai, A., et al. (*In-cell recordings by extracellular microelectrodes*.) in Nature Methods (2010) 7, 200-202. Despite successful intracellular cation and pH sensors using microelectrodes coated with ion-selective membranes by Bakker, E. & Pretsch, E. (*Nanoscale potentiometry*.) in TrAC Trends in Analytical Chemistry 27, 612-618, the intracellular electrical detection of biomolecules remains elusive. Lieber et collaborators developed a novel approach where a nanoscale field effect transistor (nanoFET) modified with phospholipid bilayers was able penetrate a single cell and record intracellular potentials (Tian, B. et al. *Three-Dimensional, Flexible Nanoscale Field-Effect Transistors as Localized Bioprobes*. Science 329, 830-834, doi:10.1126/science.1192033, 2010). However no electrical sensors were employed to detect biomolecular interaction inside a single cell.

STING ("Signal transduction by ion nano-gating") technology has also been shown capable of detecting DNA, proteins and mycotoxins in a sample (Fu, Y., et al., *Nanopore DNA sensors based on dendrimer-modified nanopipettes*. Chem Commun (Camb), (2009), 4877-4879, doi:10.1039/b910511e; Umehara, S., et al., *Label-free biosensing with functionalized nanopipette probes*. Proceedings of the National Academy of Sciences (2009) 106, 4611-4616, doi:10.1073/pnas.0900306106; Actis, P., et al., *Ultrasensitive mycotoxin detection by STING sensors*. Biosensors and Bioelectronics (2010)26, 333-337). Based on a functionalized quartz nanopipette, STING technology does not require any nanofabrication facility; each probe can be easily and inexpensively tailored at the bench. Receptor molecules can be incorporated using well established surface chemistries. Besides biosensing, nanopipette platform were used to study single molecule biophysics, controlled delivery inside individual cells, and to image cells at the nanoscale (Clarke, R. W., et al., *Trapping of proteins under physiological conditions in a nanopipette*. Angew Chem Int Ed Engl (2005), 44, 3747-3750, doi:10.1002/anie.200500196; Laforge, F. O., et al., *Electrochemical attosyringe*. Proceedings of the National Academy of Sciences (2007), 104, 11895-11900, doi:10.1073/pnas.0705102104; Klenerman, D. & Korchev, Y. *Potential biomedical applications of the scanned nanopipette*. Nanomedicine (Lond) (2006), 1, 107-114, doi:10.2217/17435889.1.1.107). Vitol and coworkers developed a SERS active carbon nanopipette for intracellular analysis (Singhal, R. et al. *Small diameter carbon nanopipettes*. Nanotechnology, (2010), 015304). SERS functionality was added by incorporating gold nanoparticles on the outer surface pipette tip. SERS spectra obtained with the nanopipette inserted within the nucleus show typical features associated with DNA.

However, there remains a need in the art for a nanopipette biosensor that can operate within a living cell.

Specific Patents and Publications

Karhanek et al. in US Patent Application Publication 2010/0072080, published on Mar. 25, 2010, disclose methods and devices comprising a functionalized nanopipette for biomolecular detection, including of peptides and proteins.

Umehara et al. in Proceedings of the National Academy of Sciences, vol 106, pages 4611-4616, Mar. 24, 2009, disclose a label-free, real-time protein assay using functionalized nanopipette electrodes.

Ying, Liming in Biochemical Society Transactions, vol 37, pages 702-706, 2009, reviews nanopipettes and their use in nanosensing and nanomanipulation of ions, molecules (including biomolecules) and cells.

Actis, P., et al. in Bioanalytical Reviews 1, 177-185, doi:10.1007/s12566-010-0013-y (2010) review applications of nanopipette technology as electrochemical biosensors for nucleic acids and small proteins.

Hansma et al. U.S. Pat. No. 4,924,091 issued May 8, 1990, entitled "Scanning Ion Conductance Microscope," describes a scanning ion conductance microscope, SICM, which can image the topography of soft non-conducting surfaces covered with electrolytes by maintaining a micropipette probe at a constant conductance distance from the surface.

BRIEF SUMMARY OF THE INVENTION

The following brief summary is not intended to include all features and aspects of the present invention, nor does it imply that the invention must include all features and aspects discussed in this summary.

In certain aspects, the present invention pertains to an apparatus for depositing onto a substrate a liquid in a predefined location having submicron features, comprising: (a) a multi-barreled nanopipette, wherein two barrels have inside them a first and second electrode, said first electrode in a barrel adapted to hold said liquid in contact with an electrode in that barrel and connected to a circuit for controlling a voltage between said first and second electrodes during use; (b) an xyz controller attached to said nanopipette for effecting mechanical movement of the nanopipette in submicron x and y steps, and effecting movement of said nanopipette in a z direction, said xyz controller further having electronic controls for controlling said mechanical movements according to user defined control; and (c) said circuit for controlling a voltage connected to said electronic controls so that said circuit applies an ejection voltage to said liquid at a desired location in said predefined location where liquid in said nanopipette is to be deposited and removing said ejection voltage when the xyz controller effects mechanical movement of the nanopipette away from the desired location in said predetermined location where liquid is to be deposited.

In certain aspects of the invention, a substrate may have a uniform layer on which the patterning material is deposited. The patterning material can define an adhesion material for cell growth.

In certain aspects of the invention, the apparatus comprises a circuit for controlling voltage that comprises a low noise amplifier for pipette bias and current measurement of ionic current through the first barrel. The apparatus may further comprise a piezoelectric actuator for submicron control of the xyz controller. The apparatus further may comprise a programmable device, such as a computer or an FPGA for user input of said predefined location. The FPGA may be programmed for depositing spots in a pattern, so that cells grow in a predefined pattern. The FPGA may be programmed to inject a cell at a predetermined location. This location may be adapted to hold an individual cell in place so that it can be scanned and injected. The predetermined location may be an organelle within a cell, such as a nucleus or a mitochondrion.

In certain aspects of the invention, the cell substrate is adapted to hold cells by having therein defined cavities for receiving an individual cell in a single cavity. The cavity may have through-holes for applying negative pressure to hold a cell in a cavity. The cavity may comprise an electrode for attracting a cell to the cavity. The cavity may serve to hold an individual cell in a fixed position while a nanopipette is contacted with the cell, and also while it is injected into the cell.

Certain aspects of the invention comprise a method for depositing onto a substrate a liquid in a predefined pattern having submicron features, comprising: (a) placing a liquid to be deposited into a multi-barreled nanopipette, wherein at least two barrels of said multibarreled pipette have inside them a first and second electrode, said first electrode in a barrel adapted to hold said liquid in contact with an electrode in that barrel and connected to a circuit for controlling a voltage between said first and second electrodes during use; (b) actuating an xyz controller attached to said nanopipette for effecting mechanical movement of the nanopipette in submicron x and y steps, and effecting movement of said nanopipette in a z direction, said xyz controller further having electronic controls for controlling said mechanical movements according to a user defined pattern, said actuating thereby moving the nanopipette in said predefined pattern; and (c) using said circuit for controlling a voltage connected to said electronic controls so that said circuit applies an ejection voltage to said liquid at a desired location in said predefined pattern where liquid in said nanopipette is to be deposited and removing said ejection voltage when the xyz controller effects mechanical movement of the nanopipette away from the desired location in said predetermined pattern where liquid is to be deposited. These methods may be further carried out according to specific embodiments of the apparatus defined above.

Certain aspects of the invention comprise a method for injecting a material into a cell on a substrate, using apparatus as described above. These methods may comprise the step of immobilizing said cell on said substrate by placing said cell in a cavity in the substrate, said cavity sized to hold only an individual cell. Immobilizing may comprise applying a voltage to the cell to hold it in place, or applying a pressure differential across said cavity to aid in immobilizing said cell. The cell may be injected with a variety of materials that are in a bore of the nanopipette, including a polynucleic acid, an antibody, and a dye.

Certain aspects of the invention comprise an apparatus for measuring an analyte within a single cell, comprising: (a) a nanopipette having a barrel containing a first electrode, said first electrode adapted to hold said analyte in contact with a second, reference electrode in a liquid contacting said cell and connected to a circuit for controlling a voltage between said first and second electrodes during use; (b) an xyz controller attached to said nanopipette for effecting mechanical movement of the nanopipette in submicron x and y steps, and effecting movement of said nanopipette in a z direction, said xyz controller further having electronic controls for controlling said mechanical movements according to user defined control; and (c) said nanopipette tip having an analyte binding material immobilized on an interior surface within said cell near a tip. This type of sensing an analyte with a functionalized nanopipette tip also involves inserting the tip into or in the vicinity of an individual cell. The tip is functionalized with an analyte binding material such as a protein or a polynucleic acid intended to bind specifically to the analyte being detected or measured. Binding of the analyte affects current flow through the nanopore at the tip of the nanopipette. A protein for sensing the analyte may be immobilized at the tip by sulfo-SMCC linked to a PLL coating on an interior surface of the nanopipette. The nanopipette tip may be functionalized with antibodies or aptamers, or receptors to a ligand to be detected. The apparatus may be used in an immunoassay inside of a single living cell.

Thus an apparatus of the present invention can be created in a number of ways for different applications. In each case, the device contains a nanopipette attached to a sensitive xyz controller.

In certain aspects, the present invention comprises an apparatus for manipulating individual cells on a substrate, comprising: (a) a multi-barreled nanopipette, having (i) a first barrel containing a first electrode arranged to be in contact with a liquid in the first barrel; (ii) a second barrel adjacent the first barrel containing a second electrode arranged to be in contact with a liquid in the second barrel; and (iii) an amplifier connected to said first electrode for controlling a voltage between said first and second electrodes; (b) an xyz controller attached to said multi-barreled nanopipette for effecting mechanical movements of the multi-barreled nanopipette in submicron x and y steps, and effecting movement of said multi-barreled nanopipette in a z direction towards or away from the substrate, said xyz controller further having electronic controls for controlling said mechanical movements according to user defined control; and (c) a circuit for controlling voltage between said first electrode and said second electrode and for applying an ejection voltage to said first electrode, said voltage sufficient to eject liquid from the first barrel at a desired location where liquid in said nanopipette is to be ejected and removing said ejection voltage at least when the xyz controller effects mechanical movement of the nanopipette away from the desired location.

In certain aspects, the present invention comprises an apparatus wherein the detecting is detecting of specific oncoproteins in a single living cell.

In certain aspects, the present invention comprises an apparatus wherein said circuit for controlling voltage comprises a low noise amplifier for providing a pipette bias voltage and for and current measurement of ionic current through the first barrel.

In certain aspects, the present invention comprises an apparatus having a piezoelectric actuator for submicron control of the xyz controller. In certain aspects, the present invention comprises a field-programmable gate array (FPGA) for user input to determine said desired location. In certain aspects, the present invention comprises an apparatus wherein said FPGA is programmed for depositing spots in a pattern on said substrate. In certain aspects, the present invention comprises an apparatus wherein said FPGA is programmed to inject a cell which is at a predetermined location on said substrate. In certain aspects, the present invention comprises an apparatus wherein said FPGA is programmed to inject an organelle within said cell.

In certain aspects, the present invention comprises an apparatus operatively connected to a substrate adapted to contain a plurality of individual cells, one cell each, in individual locations. In certain aspects, the present invention comprises a substrate that has cavities defined therein for receiving an individual cell in a single cavity. In certain aspects, the present invention comprises an apparatus wherein the substrate comprises through-holes for applying negative pressure to hold a cell in a cavity. In certain aspects, the present invention comprises an apparatus wherein the cavity comprises an electrode for attracting a cell to the cavity.

In certain aspects, the present invention comprises a method for depositing a liquid in a predefined pattern having submicron features, comprising the steps of: (a) placing a liquid to be deposited into a multi-barreled nanopipette having (i) a first barrel containing a first electrode arranged to be in contact with a liquid in the first barrel; (ii) a second barrel adjacent the first barrel containing a second electrode arranged to be in contact with a liquid in the second barrel; and (iii) an amplifier connected to said first electrode for controlling a voltage between said first and second electrodes; (b) actuating an xyz controller attached to said multi-barreled nanopipette for effecting mechanical movements of the multi-barreled nanopipette in submicron x and y steps, and effecting movement of said multi-barreled nanopipette in a z direction towards or away from the substrate, said xyz controller further having electronic controls for controlling said mechanical movements according to user defined control; and (c) using a circuit for controlling voltage between said first electrode and said second electrode and for applying an ejection voltage to said first electrode to eject liquid from the first barrel at a desired location where liquid in said nanopipette is to be ejected and removing said ejection voltage when the xyz controller effects mechanical movement of the nanopipette away from the desired location, whereby said liquid is deposited in said predetermined pattern.

In certain aspects the invention comprises a method as described above wherein said liquid comprises a cell adhesion material for allowing attachment of cells on a substrate only at areas of deposited cell adhesion material. In certain aspects the invention comprises a method as described above wherein said cell adhesion material is laminin. In certain aspects the invention comprises a method as described above wherein the substrate comprises a uniform polymer top surface. In certain aspects the invention comprises a method as described above wherein said liquid comprises a cell adhesion material for allowing attachment of cells on the substrate only at areas of deposited cell adhesion material, and further comprising the step of applying to the substrate adherent cells to be cultured, whereby said cells only adhere to regions having cell adhesion material.

In certain aspects the invention comprises a method as described above wherein regions having cell adhesion material are at a density of about at least 10 spots per 100 square micrometers. In certain aspects the invention comprises a method as described above wherein the method is used to deposit different material from different barrels of the nanopipette.

In certain aspects the invention comprises a method as described above wherein the nanopipette is made of quartz and has an opening of about 20 to 100 nm.

In certain aspects, the present invention comprises a method for injecting a material into a selected cell on a substrate, comprising the steps of: (a) placing a liquid to be injected into a multi-barreled nanopipette, having (i) a first barrel containing a first electrode arranged to be in contact with a liquid in the first barrel; (ii) a second barrel adjacent the first barrel containing a second electrode arranged to be in contact with a liquid in the second barrel; and (iii) an amplifier connected to said first electrode for controlling a voltage between said first and second electrodes; (b) actuating an xyz controller attached to said multi-barreled nanopipette for effecting mechanical movements of the multi-barreled nanopipette in submicron x and y steps, and effecting movement of said multi-barreled nanopipette in a z direction towards or away from the substrate, said xyz controller further having electronic controls for controlling said mechanical movements according to user defined control; and (c) using a circuit for controlling voltage between said first electrode and said second electrode and for applying an ejection voltage to said first electrode to eject liquid from the first barrel at a desired location where liquid in said nanopipette is to be ejected and removing said ejection voltage when the xyz controller effects mechanical movement of the nanopipette away from the desired location, whereby said liquid is injected into said cell.

In certain aspects the invention comprises a method as described above further comprising the step of immobilizing said cell on said substrate by placing said cell in a cavity in the substrate, said cavity sized to hold only an individual cell.

In certain aspects the invention comprises a method as described above further comprising the step of applying a pressure differential across said cavity to aid in immobilizing said cell.

In certain aspects the invention comprises a method as described above wherein said material injected is selected from the group consisting of a polynucleic acid, an antibody, and a dye.

In certain aspects, the present invention comprises a apparatus for detecting an analyte in an individual cell on a substrate, comprising: (a) a nanopipette having a barrel containing a first electrode, said first electrode adapted to hold said analyte in contact with a second, reference electrode in a liquid contacting said cell and connected to a circuit for controlling a voltage between said first and second electrodes during use; and (b) an xyz controller attached to said nanopipette for effecting mechanical movement of the nanopipette in submicron x and y steps, and effecting movement of said nanopipette in a z direction, said xyz controller further having electronic controls for controlling said mechanical movements according to user defined control; and (c) said nanopipette tip having an analyte binding material immobilized on an interior surface within said cell near a tip.

In certain aspects, the present invention comprises an apparatus wherein said analyte binding material is a protein or a polynucleic acid.

In certain aspects, the present invention comprises an apparatus wherein the analyte binding material is a protein linked by sulfosuccinimidyl-4-(N-maleimidomethyl)cyclohexane-1-carboxylate (Sulfo-SMCC) to a poly-L-lysine (PLL) coating on said interior surface.

In certain aspects, the present invention comprises a method to detect biomolecules in a single living cell comprising: (a) positioning a functionalized nanopipette to a defined depth into the cell; (b) monitoring the current to control precise position of nanopipette near the cell membrane; (c) inserting nanopipette at high speed into the cell; (d) applying high voltage; and (e) measuring current change to detect biomolecules in the cell wherein the functionalized nanopipette is comprised in a system further comprising an amplifier for pipette bias and current measurement, a micromanipulator for control in the X, Y and Z directions, a piezo-actuator for fine control in the X, Y and Z directions, a configurable integrated circuit, a high voltage source, and a relay for switching between low voltage and high voltage.

In certain aspects the invention comprises a method as described above wherein the nanopipette is functionalized with antibodies. In certain aspects the invention comprises a method as described above wherein the nanopipette is functionalized with aptamers.

In certain aspects the invention comprises a method as described above wherein the method is used in an immunoassay in a single living cell. In certain aspects the invention comprises a method as described above wherein the nanopipette is functionalized with receptor ligands.

BRIEF DESCRIPTION OF THE DRAWINGS

FIG. 5A is a photograph that show injection of carboxyfluorescein into HeLa cells. It is a brightfield image of cells and nanopipette. Arrow indicates tip of nanopipette FIG. 5B is also a photograph of cell injection, as in FIG. 5A. FIG. 5B shows a fluorescent image of HeLa cell and nanopipette after injection.

FIG. 6A is a drawing that shows silicon nitride layer is deposited on silicon wafer. FIG. 6B is a drawing that shows deep reactive ion etch through nitride layer. FIG. 6C is a drawing that shows back side KOH etch. FIG. 6D is a drawing that shows silicon wafer bonded to glass wafer.

DETAILED DESCRIPTION OF THE PREFERRED EMBODIMENT

Overview

Figure 1:
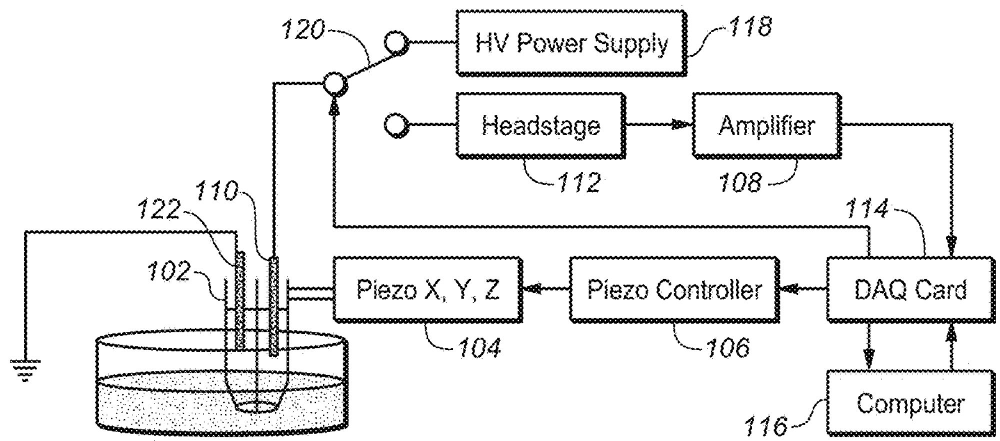
FIG. 1 is a schematic drawing of the present of deposition and cell injection system.

Disclosed herein is a system comprising a nanopipette that is attached to a robotic mechanism for three dimensional movement and useful for controlled deposition of material from the nanopipette onto a substrate for controlling cell growth, for sensing with the nanopipette tip biochemical markers at individual cell surfaces or cell interiors, or for injection of nanopipette contents into single cells. When used for chemical deposition, the small size of the nanopipette opening allows for pattern definition with resolution below the single cell level. The system further comprises using scanning ion conductance microscopy (SICM) as a basis for pattern deposition. Thus, a pattern can be predefined by the user, and subsequently laid down by controlling software, without the need for photolithography or any type of pattern preprocessing. This allows for the constant, rapid development of arbitrary user defined patterns to be quickly and efficiently evaluated with in vitro cell cultures and no loss of resolution. The disclosed system has applications in biological studies for controlling cellular attachment and growth.

SICM devices have been previously devised for imaging the topography of soft non-conducting surfaces. See, e.g. Hansma, P. K., et al., *The Scanning Ion-Conductance Microscope*. Science, 1989. 243(4891): p. 641-643. Such prior art devices use XYZ scanning, Z feedback and control logic (Z is considered to be the direction orthogonal to the surface being scanned).

Another aspect of the present invention is directed to a system comprising a nanopipette for high-throughput cell injection including methods for cell immobilization and injection. Embodiments of the invention are directed to cell injection of an arbitrary material into a cell using a nanopipette and electroosmotic injection, with minimal damage to the cell. Electroosmotic injection involves changing a voltage and ionic current across a nanopore opening to drive a compound of interest out of the nanopipette. Also disclosed are double-barrel nanopipettes for higher efficacy of ejection and cell injection.

Also disclosed is a cell sifter fabricated for immobilization of cells in a predetermined array for fully automated injection into cells. The cell sifter contains three dimensional features, such as recessed opening, that allow for the placement of single cells that may be retained in a predetermined location, preferably in an array of locations, each containing a single cell. Embodiments of this technology can be used as a tool for high throughput single-cell studies involving the introduction of material reliably into a single living cell or immunoassays of the cell interior. Alternate embodiments include immobilization of structures including polymer beads.

Also disclosed are methods and devices integrating the present nanopipette sensors with apparatus for scanning the nanopipette across a biological material. A nanopipette sensor as described here can be coupled with scanning ion conductance microscopy (SICM) to study molecular interactions inside individual living cells. Cells can be interrogated inside the growing medium without any need for fixation or pretreatments. The small size of the nanopipette with respect to the cell size combined with controlling the conditions of penetration maximizes cell viability. Applications of this technology include in vivo assay down to the single cell level. Another application is it allows for the continuous monitoring of biomolecules inside individual cells, e.g., an immunoassay to monitor protein expression. Furthermore, this technology can be employed to functional map secreted molecules from a single cell.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "nanopipette" is used herein to refer to a hollow self-supporting, inert, non-biological structure with a conical tip opening (i.e. a nanopore) of nanoscale, i.e., 0.05 nm to about 500 nm, preferably about (+ or −20%) 50 nm. The hollow structure may be glass or quartz, and is suitable for holding inside of it, or on one side of the nanopore, a fluid which is passed through the nanopore opening. The interior of the nanopipette is selected or modified to minimize nonspecific binding of analyte. The interior is sized to allow insertion of an electrode that contacts solution in the nanopipette. Nanopipettes are preferably fabricated by laser pulling of glass or quartz capillary tubes. Nanopipettes have an inner diameter on the order of 10-100 nm, an outer diameter on the order of 200-800 nm, and a typical length of about 10 μm. These dimensions are sized to suit a particular application, and control of the nanopore size is an important consideration. A "multibarrelled nanopipette" is a nanopipette that has two or more parallel bores that typically share a common wall. The bores are co-axial, typically radially spaced, but may be concentric. They may be fabricated from multibore capillary tubes, which are commercially available.

The term "nanopore" is used herein to refer to a small hole in an electrically insulating membrane that can be used as a single-molecule detector. The detection principle is based on monitoring the ionic current passing through the nanopore as a voltage is applied across the membrane. A preferred nanopore opening is between about (within 10% of) 20 and 100 nm.

The term "current detecting circuit" or "circuit for controlling a voltage" refers to known electronic circuits and devices that include a controllable amplifier and a sensitive voltage and current detector. They may comprise any sensitive device for detecting changes in current on the order of 1-10 picoamperes, based on a baseline current of 10-10000 picoamperes. The term further refers to a circuit that is time responsive and relatively temperature independent or allow for changes in temperature to be compensated for. It should have an input in a circuit where a known voltage is supplied. Sensitive detecting circuits are known, including voltage clamp amplifiers and transimpedance amplifiers. The term "voltage clamp" here refers to circuits which utilize a differential amplifier having one input connected to a variable command voltage, another input connected to a measured voltage, and a feedback circuit. The voltage clamp uses negative feedback to maintain the system at the command voltage, which in this case is a predetermined alternating signal, such as an alternating voltage signal from a signal generator. The output current follows changes in the input voltage and small changes in current can be detected.

The term "electroosmotic flow" or "electro-osmotic flow" is used herein in its conventional sense to refer to the effect of an applied electric field on the electrical double layer that forms at the surface of the nanopipette. The ions arranged at the inner surface of the nanopipette tip are forced out of the nanopipette under a sufficiently strong electric field, such that a small volume of solution is simultaneously forced from the tip. Electroosmosis ejects a liquid, while electrophoresis moves charged particles within a medium such as liquid or gel. Electrosomosis is induced by an applied potential across a capillary tube, or any other fluid conduit.

The term "laminin" is used herein in its conventional sense to refer to major proteins in the basal lamina (formerly improperly called "basement membrane"), a protein network foundation for most cells and organs. The laminins are an important and biologically active part of the basal lamina, influencing cell differentiation, migration, adhesion as well as phenotype and survival. Laminins are trimeric proteins that contain an α-chain, a β-chain, and a γ-chain, found in five, three, and three genetic variants, respectively. Laminin is vital for the maintenance and survival of tissues. Defective laminins can cause muscles to form improperly, leading to a form of muscular dystrophy, lethal skin blistering disease (junctional epidermolysis bullosa) and defects of the kidney filter (nephrotic syndrome). Laminin is used in cell culture and for studying cellular interactions with the extracellular environment. For example, Laminin-111 is a major substrate along which nerve axons will grow, both in vivo and in vitro. For example, it lays down a path that developing retinal ganglion cells follow on their way from the retina to the tectum. It is also often used as a substrate in cell culture experiments.

The term "oncoprotein" is used herein in its conventional sense to refer to a protein encoded by an oncogene; they may include viral proteins known to be associated with cancer. See, e.g. Clemens et al., "Dimerization of Human Papillomavirus E7 Oncoprotien in Vivo,' Virology 214, 289-293 (1995). The protein encoded by the viral oncogene and the corresponding, homologous protein within the host cell are both referred to herein as oncoproteins, although the cellular oncoprotein is typically larger and is present in small quantities in normal cells, and thus need not only be associated with neo-plastic states. They include myc, bc1-2, mutated p53, DEK, HPV E6, HPV E7, etc.

The term "cell adhesion material" is used herein to refer to materials such as proteins that for example, in nature, attach cells to specific compounds in the extracellular matrix (a process known as cell adhesion). Some of the amino acids in the substrate adhesion molecules (SAM) bind to components of the extracellular matrix, while others bind to integrins on the surface of the cell. Integrin molecules are composed of two chains of amino acids, one of which is connected to the actin filaments in the cytoskeleton, while the other is connected to the SAMs. This enables external activity in the extracellular matrix to affect the shape and movement of the cell. SAMs do not have to be made by the cells that bind to them. They can also link to other SAMs, influencing each other's behavior.

The term "field-programmable gate array" is used herein to refer to an integrated circuit designed to be configured by the customer or designer after manufacturing—hence "field-programmable". The field-programmable gate array (FPGA) configuration is generally specified using a hardware description language (HDL), similar to that used for an application-specific integrated circuit (ASIC). FPGAs contain programmable logic components called "logic blocks", and a hierarchy of reconfigurable interconnects that allow the blocks to be "wired together"—somewhat like many (changeable) logic gates that can be inter-wired in (many) different configurations. Logic blocks can be configured to perform complex combinational functions, or merely simple logic gates like AND and XOR. In most FPGAs, the logic blocks also include memory elements, which may be simple flip-flops or more complete blocks of memory.

The term "xyz controller" refers to a mechanical device that moves in three dimensions, known as the x and y dimension, typically a flat surface, and the z direction, typically vertical. Xyz controllers are known for use in a variety of micro-scale applications, such as an atomic probe microscope; see, e.g. U.S. Pat. No. 5,394,741 to Kajimura et al., entitled "Atomic probe microscope," for further details on an exemplary xyz controller.

The term "ejection voltage," as further described below, refers to a voltage applied in the present nanopipette between the bore, containing a solution, and an exterior solution, which voltage causes an ionic flow from the bore, i.e. ejecting an atomic species within the solution. That is, in the present device, ejection from the nanopipette bore occurs due to electroosmosis, which means it depends on the properties of the nanopipette rather than what is being ejected. The fluid is ejected from the bore that contains a positively biased electrode, relative to the counter electrode that is in the other bore. As exemplified below, a voltage between 0.1 to 100V is applied across the two bores of a double barreled nanopipette to cause ejection. The amount of ejected material depends on the time and the magnitude of the applied voltage. For purposes of illustration, low voltage is between 0.01-1V and high voltage is 1-100V. If a single bore pipette is used and a high voltage relative to an electrode outside the cell is applied, then the voltage would have to pass through the cell membrane likely causing damage. Thus, a double bore pipette is preferred over the use of a single bore pipette.

The term "low noise amplifier," or LNA as is known in the art, refers to one of a variety of amplifiers, where the amplifier is an electronic amplifier used to amplify very weak signals (for example, captured by an antenna). It is usually located very close to the detection device to reduce losses in the feedline. Typically, using an LNA, the effect of noise from subsequent stages of the receive chain is reduced by the gain of the LNA, while the noise of the LNA itself is injected directly into the received signal. Thus, it is necessary for an LNA to boost the desired signal power while adding as little noise and distortion as possible, so that the retrieval of this signal is possible in the later stages in the system. A good LNA has a low NF (like 1 dB), a large enough gain (like 20 dB) and should have large enough intermodulation and compression point (IP3 and P1 dB).

The term "piezo actuator," as is known in the art, refers to a piezoelectric transducer. The active element is basically a piece of polarized material (i.e. some parts of the molecule are positively charged, while other parts of the molecule are negatively charged) with electrodes attached to two of its opposite faces. When an electric field is applied across the material, the polarized molecules will align themselves with the electric field, resulting in induced dipoles within the molecular or crystal structure of the material. This alignment of molecules will cause the material to change dimensions. In terms of the present device, the transducer is used to accomplish fine degrees of movement on a very small scale.

The term "polynucleic acid" refers to any oligomer or polymer of single or (partially) double stranded DNA or RNA or synthetic analogs thereof; as used herein, the polynucleic acid is capable of binding to a complementary strand with specificity based on Watson-Crick base pairing.

The term "antibody" refers to any antibody or antibody fragments having binding specificity through an antigen binding portion. For example, it has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

The term "aptamer" refers to a polynucleotide or peptide that binds to a specific target molecule. Exemplary aptamers include those derived from SELEX protocols, as described e.g. in Gold et al. U.S. Pat. No. 5,567,588 entitled "Systematic evolution of ligands by exponential enrichment: Solution SELEX;" SELEX-identified oligonucleotides containing modified nucleotides are described, e.g., in U.S. Pat. No. 5,660,985, which describes oligonucleotides containing nucleotide derivatives chemically modified at the 2' position of ribose, 5 position of pyrimidines and 8 position of purines, U.S. Pat. No. 5,756,703 which describes oligonucleotides containing various 2'-modified pyrimidines and U.S. Pat. No. 5,580,737 which describes highly specific oligonucleotides containing one or more nucleotides modified with 2'-amino (2'-NH2), 2'-fluoro (2'-F) and/or 2'-O-methyl (2'-OMe) substituents. Peptide aptamers are combinatorial recognition proteins. Peptide aptamers have been selected, using yeast two-hybrid methods, to bind to a wide range of cellular, viral and bacterial target proteins involved in a variety of regulatory pathways, as described in Colas, The eleven-year switch of peptide aptamers," J. Biol. 7(1) 2 (2008). A peptide aptamer is described in US 20090318363 entitled "Peptide aptamer for neutralizing the binding of platelet antigene specific antibodies and diagnostic and therapeutic applications containing the same."

The term "dye" refers to a composition that imparts color to another composition of matter or to a mixture. Preferred dyes are fluorogenic compounds. Also included in this definition are energy transfer dyes. Also included are xanthene dyes, asymmetric benzoxanthene dyes, rhodamine dyes, fluorescein dyes, 4,7-dichlororhodamine dyes, 4,7-dichlorofluorescein dyes, carboxyfluorescein dyes, carboxyrhodamine dyes, carboxy R110 dyes, carboxy R6G dyes, carboxy-X-rhodamine dyes, cyanine dyes, phthalocyanine dyes, squaraine dyes, and Cy5, as defined or used in U.S. Pat. No. 6,335,440, which is also hereby incorporated by reference.

General Method and Apparatus

In a first aspect, the present invention comprises a system for depositing a user defined pattern on an arbitrary substrate for the purpose of controlled cell adhesion and growth. The approach has the advantage that controlled deposition can be performed onto an unfunctionalized surface in an ambient environment. Such patterned substrates are used for successful cell cultivation and good attachment and viability to predefined patterns.

Device as Adapted for Substrate Patterning

The system comprises a computer controlled feedback system exemplified by a system for scanning ion conductance microscopy (SICM). The basic operation of SICMs is well understood in art (See, for example, Hansma, P. K., et al., *The Scanning Ion-Conductance Microscope*. Science, 1989. 243(4891): p. 641-643; Prater, C. B., et al., *Scanning Ion-Conductance Microscope And Atomic Force Microscope*. Scanning, 1990. 12(1): p. 50-52). Briefly, the basic SICM consists of a single pipette back-filled with an electrolyte and immersed in an electrolytic bath. An electrode is placed in the nanopipette and a ground electrode is placed at some distance away in the bath. As the opening of a nanopipette approaches a substrate, normal to the surface, the current flowing through the pipette orifice for a given will be reduced by "current squeezing". This drop in current can act as a feedback signal to control the height of the nanopipette which can be controlled at a predefined distance above the surface. If the nanopipette is then scanned across a surface a topographical image can be rendered of the substrate.

As explained below, features of this device may be incorporated into related devices for injecting a single cell, or for measuring molecular binding within a single cell.

FIG. 1 is a schematic drawing of the present device, which can be included in a modified SICM (scanning ion conductance microscopy) custom built for cell injection according to the present invention. The present device relies on feedback-controlled positioning in the z-direction for fine control over penetration of the membrane. According to the present device, a double-barrel nanopipette 102 is attached to the xyz controlling portion, comprising a piezo x,y,z controller 104 and a piezo controller 106 operatively connected to the piezo x,y,z controller. The piezo xyz controller 104 is used for very fine movement, and is mounted on a step-motor micromanipulator (not shown) for more coarse movement. A piezo control circuit is connected through a DAQ card 114 to a computer 116. The DAQ is connected to an electronic sensor and amplifier connected to an electrode 110 within the nanopipette. (A reference electrode 122 in the second bore, fused to the first bore, is connected to ground, as shown.) The SICM module further comprises a low-noise amplifier 108 (for example, Axopatch 200B, Molecular Devices, Sunnyvale, Calif.) for pipette bias and current measurement. The amplifier is connected through DAQ card 114 to an electrode 110 within the nanopipette, as shown. It includes a headstage amplifier 112 feeding into the amplifier 108, which outputs to a DAQ (data acquisition) card 114. Suitable DAQ cards are commercially available. For example, DAQ boards (made by National Instruments) are multi function plug-n-play, analog and digital input/output boards consisting of a onboard timer, 12 bit analog to digital converter (ADC) with 8 channel input, 2 digital to analog converters (DAC) and 24 TTL level logic inputs.

Figure 2:
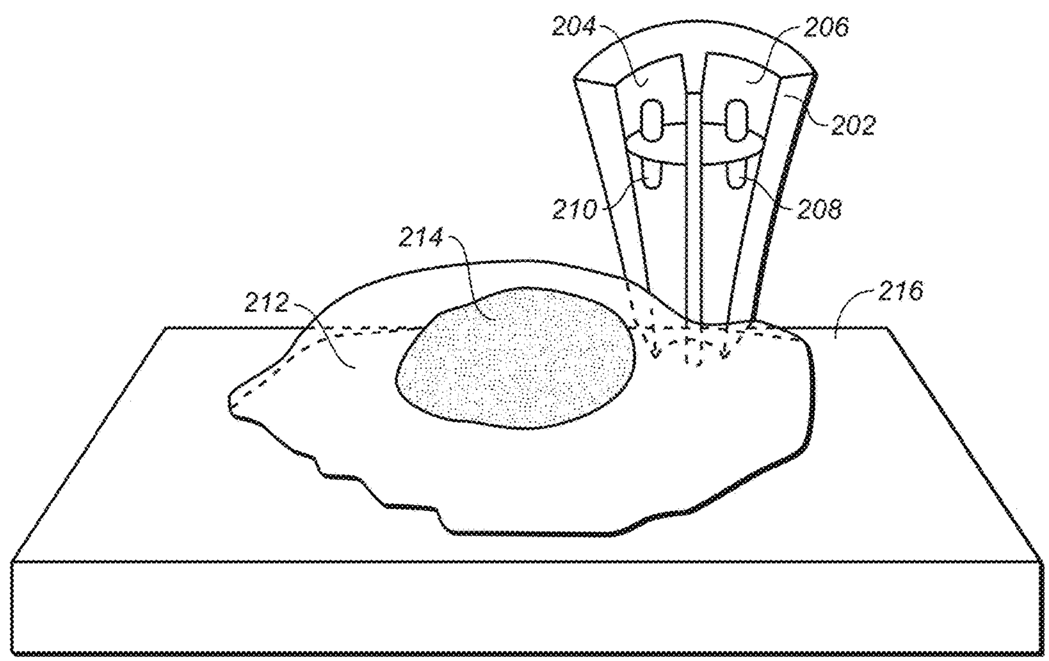
FIG. 2 is a schematic drawing of a cell penetration using a double-barrel pipette with the present system.

The DAQ card (which is a FPGA) interfaced with a computer controller 116, also is connected to the circuitry for controlling movement of the nanopipette through a piezo xyz controller. One xyz controller is a micromanipulator 106 (for example, MP-285) for coarse control in the X, Y, and Z directions. This is then coupled to a piezo actuator 104 for fine control (positionable within 2-3 nm) in the X, Y, and Z directions, and a FPGA for hardware control of the system. The system is further modified with a low-noise high voltage source 118 (for example, Model 2100 Isolated Pulse Stimulator, A-M Systems), and a custom relay 120 for switching between the low voltages (about 0.01-1 V) required for feedback control and the high voltages needed for electrophoretic material ejection (FIG. 2). The system is controlled using user coded software written, for example, in LabVIEW. LabVIEW is available from National Instruments Corporation, and LabVIEW is a graphical programming environment used to develop sophisticated measurement, test, and control systems using intuitive graphical icons and wires that resemble a flowchart. Thus a user can design a predetermined pattern of nanopipette xyz motion, as well as voltage changes to cause ejection of material at a predetermined location, for a predetermined length of time. LabView also permits a predetermined pattern to be loaded into the software. LabView or other conventional software is supplied with the present device to control the sensing and ejection from the nanopipette, and the motion of the nanopipette.

Material ejection from a bore of the pipette is performed using a double-barrel nanopipette back filled with an appropriate buffer and the material of interest. Suitable buffers include phosphate, citrate or any other buffers routinely used in molecular studies. An ejection voltage is applied between electrodes 110 and 122 by changing the voltage coming from the power supply 118.

A variety of electrolyte solutions may be used in the nanopipette bore to affect ejection of the material of interest. In the case of cell patterning, the material of interest will be used to create a cell adhesion pattern. As described below, the material of interest may be varied, depending on the application. The material of interest is suspended in the bore in an electrolyte solution, which, as is known, contains dissolved electrolytes, i.e., free ions. Typical ions include sodium, potassium, calcium, magnesium, chloride, phosphate and bicarbonate. Other ionic species may be used. The material of interest will typically be liquid, in that it will comprise the material of interest, and the ions in solution. The material of interest itself may be an electrolyte, such as human plasma or other body fluids, solutions, water samples and so on. The electrolyte should carry an ionic current; about 10-100 mM, preferably about 100 mM of positive and negative ionic species are thought to be required for this function. The present device may employ either the same or different electrolytes in the nanopipette interior and in the sample material. A variety of salts may be used in the electrolyte solution. They are composed of cations (positively charged ions) and anions (negative ions) so that the product is electrically neutral (without a net charge). These component ions can be inorganic such as chloride ($Cl^-$), as well as organic such as acetate ($CH_3COO^-$) and monatomic ions such as fluoride ($F^-$), as well as polyatomic ions such as sulfate ($SO_4^{2-}$). There are several varieties of salts. Salts that hydrolyze to produce hydroxide ions when dissolved in water are basic salts and salts that hydrolyze to produce hydronium ions in water are acid salts. Neutral salts are those that are neither acid nor basic salts. Molten salts and solutions containing dissolved salts (e.g. sodium chloride in water) are called electrolytes, as they are able to conduct electricity.

Material of interest to be ejected includes, but is not limited to, small molecules, metabolites, nucleic acids, oligonucleotides, peptides, amino acids, dyes, polymers, nanoparticles Nanopipettes may be fabricated using quartz. Double-barrel pipettes offer the advantage of forming a small meniscus across the tip of the pipette negating the need for an external ground electrode as is common with single-barrel pipettes. Additionally, because the circuit is completed between the two barrels of the pipette the tip can function as a SICM in air, thus allowing the tip of the nanopipette to approach a dry surface. It has been previously shown by Rodolfa et al in 2005 ("*Two-component graded deposition of biomolecules with a double-barreled nanopipette*." in Angewandte Chemie-International Edition, 44: p. 6854-6859) that material can be ejected from the tip of a nanopipette using electroosmotic forces and relatively high voltages. The nanopipette is preferably formed of fused silica or amorphous quartz, which is less expensive than crystalline quartz. Crystalline quartz may, however, be utilized. Ceramics and glass ceramics and borosilicate glasses may also be utilized but accuracy is not as good as quartz. The term "quartz" is intended and defined to encompass that special material as well as applicable ceramics, glass ceramics or borosilicate glasses. It should be noted that various types of glass or quartz may be used in the present nanopipette fabrication. A primary consideration is the ability of the material to be drawn to a narrow diameter opening. Alternatively, nanopipettes may be fabricated from other non-conductive material such as other silicon oxides, metal oxides, (e.g. aluminum), carbon (See, e.g. U.S. Pat. No. 7,597,941, Tubular carbon nano/micro structures and method of making same), etc.

In some embodiments, the system is used for cell patterning on a substrate. Patterning is controlled using software programmed to control nanopipette height and position. A predefined pattern is loaded into the software. At the prescribed areas, the nanopipette is slowly lowered to the surface of the substrate to be patterned. Once the meniscus of the pipette is in contact with the substrate the relay isolates the amplifier, and applies high voltage for a prescribed amount of time. After the elapsed time, the tip is quickly retracted, the voltage across the pipette tip is discharged through a resistor to ground, and the amplifier is reconnected to the pipette. The tip is then moved to the next point and the process is repeated until an entire pattern is deposited. The rate of ejection is dependent both on applied voltage and on the duration of the applied voltage (see volume ejected versus time graph in FIG. 3).

Figure 4A:
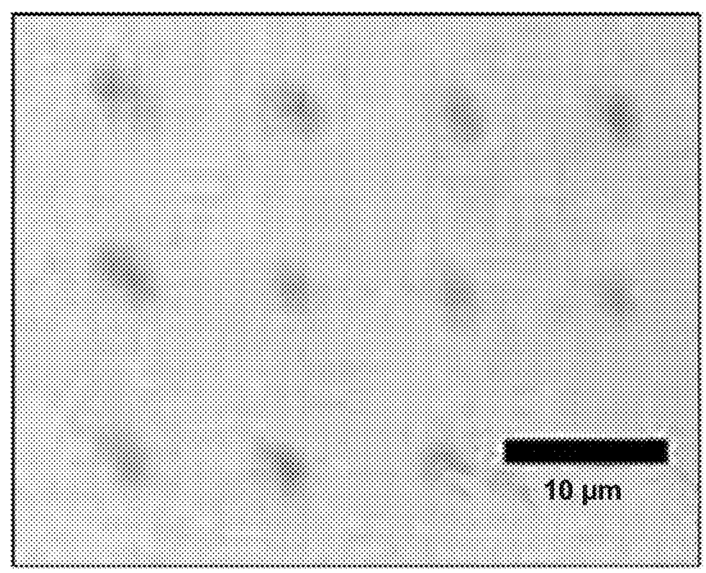
FIG. 4A is a top view photograph that shows an array of patterned spots.
Figure 4B:
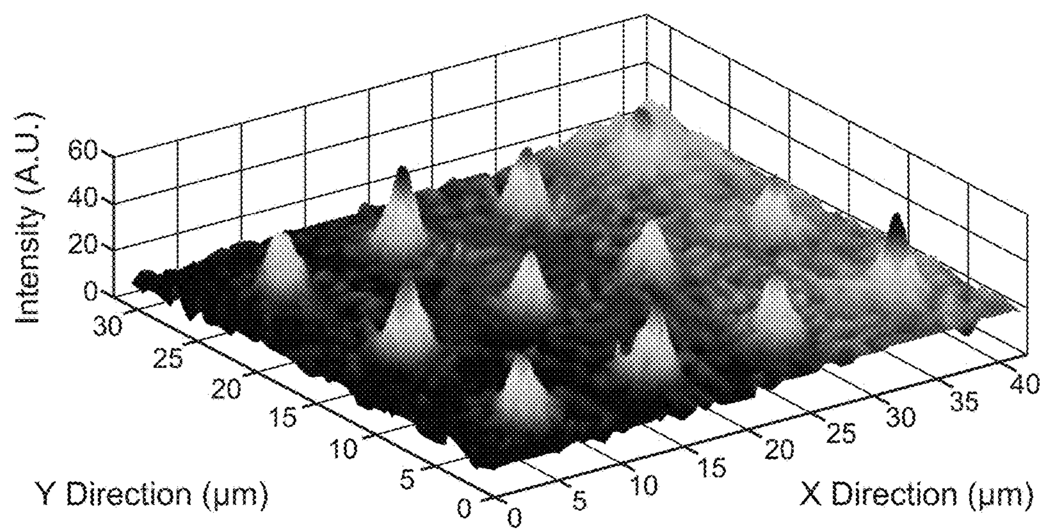
FIG. 4B is a pseudo-3-D graph of fluorescence image of an array of patterned spots using sulforhodamine.

Using the presently described apparatus, volumes as low as between 50 pL/s to 100 pL/s may be ejected from the nanopipette. Volumes can be even lower than these amounts, but they would be beyond the resolution of optical microscopes. Ejection volumes were determined by ejecting onto a suitable polymer surface in a bath of oil, for example mineral oil. Suitable liquids for contact between the tip and the substrate include organic liquid polymers (e.g. oil) and silicon-based polymers, e.g. silicones. An example of silicone is polydimethylsiloxane. A hemispherical shape of the oil drop was assumed for the volume calculations. Ejection volumes appear to be linear with the time of applied voltage. Spot sizes as small as 3 μm in diameter may be deposited. FIG. 4 shows an example of an array of patterned spots of sulforhodamine wherein the mean spot diameter is 4±0.8 μm. Results presented here are representative of individual nanopipettes; the parameters are obtained through linear fits to these data and can vary between nanopipettes. Nevertheless for standardized array printing, each nanopipette can be easily calibrated by ejecting droplet in oil. Additionally, by reversing the bias across the barrels, different material can be controllably ejected from different barrels. By loading each barrel with a separate material a multilayer pattern can be laid down in a pre-registered fashion, in a single patterning run.

Patterns on the substrate where cells are to be attached for culture may be defined on the substrate by using proteins, polymers including organic polymers, or biopolymers. Patterning is preferably used to define a number of discrete areas where separate cell growth can take place. Examples of patterning materials include, but are not limited to polylysine, bovine berum albumin (BSA), and surface adhesion molecules, e.g. fibronectin or laminin. Pattern deposition may be confirmed by mixing quantum dots with the electrolyte solution. Patterns may be assessed using, for example, fluorescence microscopy to visualize deposition, and check for errors in printing. The substrate, upon deposition, is then washed in a self masking step. Suitable buffers with masking molecules may be used for the washing step. Examples of molecules used for masking include bovine serum albumin (BSA). After pattern definition the substrate may be immersed in cell culture media. Cells may be dispersed in media and allowed to settle onto the substrate. After several hours of incubation cells are gently rinsed with pre-warmed culture media to remove any cells not firmly attached to the substrate. Cell attachment is assessed both qualitatively and quantitatively.

Cell Injection

In another embodiment, the present nanopipette system is used for electro-osmotic injection of material into a single living cell in a high-throughput manner and with minimal damage to the cell. An advantage of the approach is the highly automated nature of the injection, precise control of injection volumes, and the high cell viability. Further, a cell sifting device is presented below for cell immobilization increasing the potential for full system automation.

Figure 3:
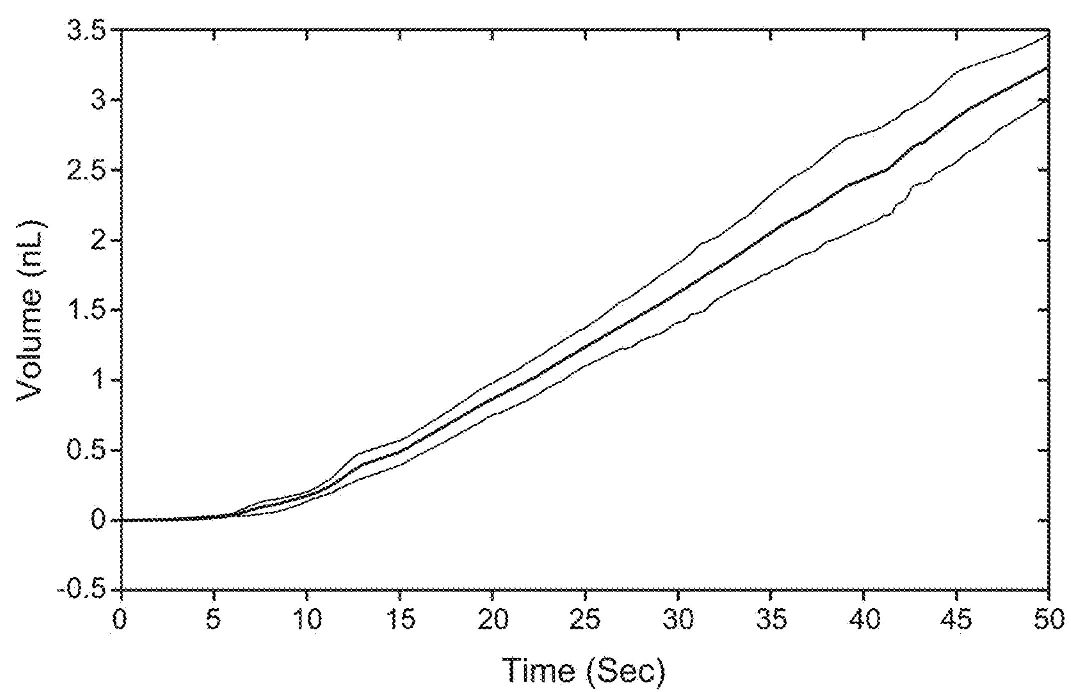
FIG. 3 is a graph showing volume of liquid ejected from a nanopipette tip over time. As indicated in the graph, the ejection rate is linear over time.

Cell injection may be performed using a double-barrel nanopipette (shown in FIG. 2) back filled with a suitable buffer and material to be injected. Suitable buffers include phosphate, citrate or any other buffers routinely used in molecular biology studies. Material to be injected includes, but is not limited to, small molecules, metabolites, nucleic acids, oligonucleotides, peptides, amino acids. FIG. 2 illustrates cell penetration using a double-barrel pipette 202, having barrels 204, 206 and electrodes 208, 210 in the barrels, one in each barrel. The pipette 202 will be attached to a piezoelectric controller as shown in FIG. 1. Double-barrel pipettes offer the advantage of allowing one barrel to be biased relative to the other barrel which can act as a ground electrode (see electrode 122 in FIG. 1) negating the need for an external ground electrode as is common with single-barrel pipettes. This has the further advantage of eliminating any electroporative effects which may occur with a single-barrel pipette and external ground electrode. The rate of ejection from the tip of a nanopipette is dependent both on applied voltage and on the duration of the applied voltage (FIG. 3). Ejection volumes appear to be linear with the time of applied voltage, which was 100V, with the pipette tip immersed in mineral oil. Mineral oil was used solely for calibration purposes by measuring the droplet size of ejected material. The mineral oil contains the ejected material since aqueous solutions are not soluble in mineral oil.

Figures 5A, 5B:
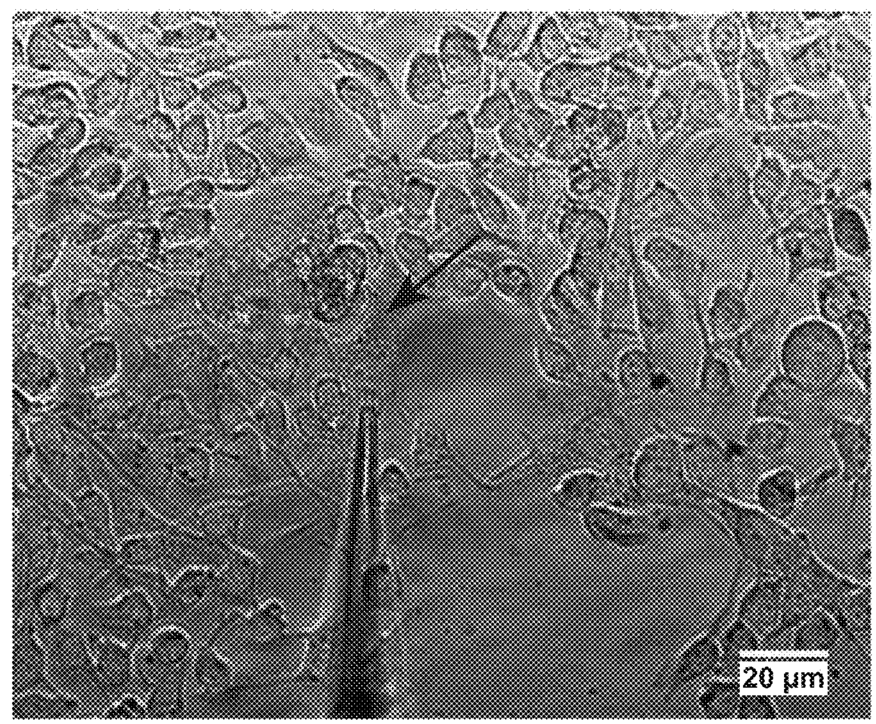
FIG. 5A-B is a series of photographs showing the present nanoinjection device.

Injection of material into cell 212 from barrel 202 connected to the power supply 118 is performed using the circuit described above in FIG. 1 and controlled using custom software. Injection is shown as taking place in the cytoplasmic region of cell 212, but injection into an observed nucleus 214 could also be accomplished. The cell rests on a solid support 216, which may be created as shown in FIG. 6. Cells including bacterial, fungal, animal, mammalian cells or cells from cell lines may be used for injection purposes. Injection is accomplished by slowly lowering the nanopipette to within between 50 to 200 nm, preferably ~100 nm, of the cell membrane where it enters feedback and is stopped. The nanopipette is then quickly lowered between 0.5 to 2 μm, preferably between 0.9-1.2 μm penetrating the cell membrane. The speed of the nanopipette while lowering may be between 50 to 200 μm/s, preferably more than 80 μm/s. The low-voltage feedback system is disconnected from the nanopipette and a high-voltage source is connected by high-voltage relay for a predetermined amount of time. The low voltages for the feedback include voltages less than 2V, preferably less than 1V. The high voltages for the feedback include voltages more than 0.5V, preferably more than 1V. Two different power supplies are utilized; one for positioning the pipette that has a power supply ranging from −1 to +1V and another for injecting that ranges from −100V to +100V. Typical cell injections range from about 5-30V, but these can be varied as long as the ejection is reproducible and the voltage does not damage the cell. The nanopipette is then discharged through a resistor and the nanopipette is retracted at high-speed. FIG. 5 shows an example of injection of a dye carboxyfluorescein into a HeLa cell. No cell damage is immediately visualized, and confinement of fluorescence is confined within the cell walls for several minutes (FIG. 5).

Cell Substrate Patterning

Another aspect of the present invention is directed to a cell sifter designed and fabricated for the immobilization of cells or molecular structures including beads in an ordered array. By immobilizing cells in an ordered array, the SICM can be controlled to address each element of the array sequentially, reducing the need for an operator to individually inject each cell separately. The sifter is fabricated using standard semiconductor fabrication technology (FIG. 6A-E). Briefly, a 500 to 1000 nm layer, preferably ~750 nm layer of a silicon salt (for example, silicon nitride) 602 is deposited onto the surface of a silicon wafer 604. The silicon wafer may be between 200 to 1000 μm thick, preferably between 300-600 μm thick. 1 to 5 μm, preferably 2-3 μm holes 606 are etched through the silicon salt layer in an array with a suitable pitch using a reactive ion etch. A suitable pitch is more than 50 μm, preferably around 100 μm pitch. Fiduciary marks (not shown) are etched into one corner of the array which can be used for SICM alignment. The wafer backside 608 is then etched by a suitable alkali (for example, sodium hydroxide or potassium hydroxide) to define a chamber 610 underneath the holes, as well as a channel 612 for the application of negative pressure to the chamber. The silicon wafer is then bonded to a glass wafer 614 sealing both the etched chamber and channel. The device is designed symmetrically so that two arrays are present at opposite ends of the device. The device is completed by breaking out the silicon salt layer on one array and attaching a barb 616 on which to attach a vacuum line. Around the other array a plastic ring 618 is attached with a suitable polymer to act as a cell culture chamber allowing cells to be immersed in cell culture media. Suitable polymers include organic polymers including silicon polymers e.g., silicones. An example of a silicone is polydimethylsiloxane. The device can be used to immobilize molecules including, but not limited to, polymers. Molecules may be comprised in beads 620. The cells or molecules are immobilized by applying negative pressure to the device through-holes. The cells would be placed in an array defined by the holes, as shown by exemplary beads 620.

Figure 6A:
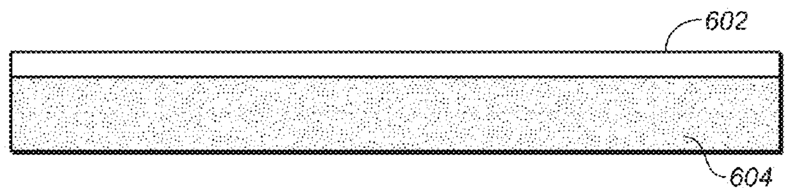
FIG. 6A-D is a series of drawings that show cell sifter fabrication.
Figure 6B:
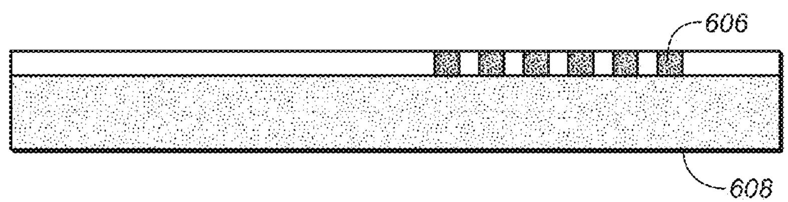
Figure 6C:
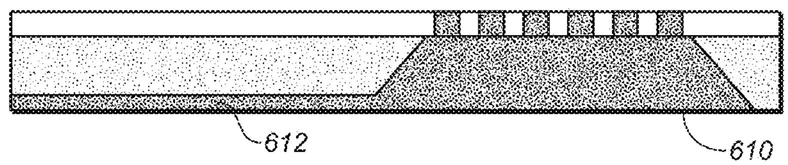
Figure 6D:
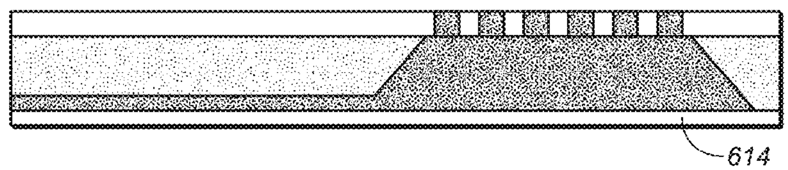
Figure 6E:
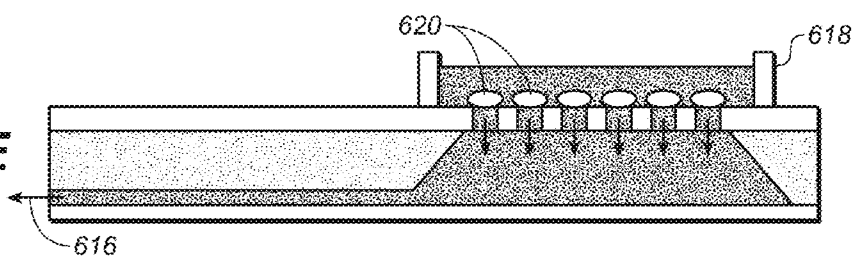
FIG. 6E is a drawing that shows that, in the final device, a plastic ring is attached to surface.
Figure 7:
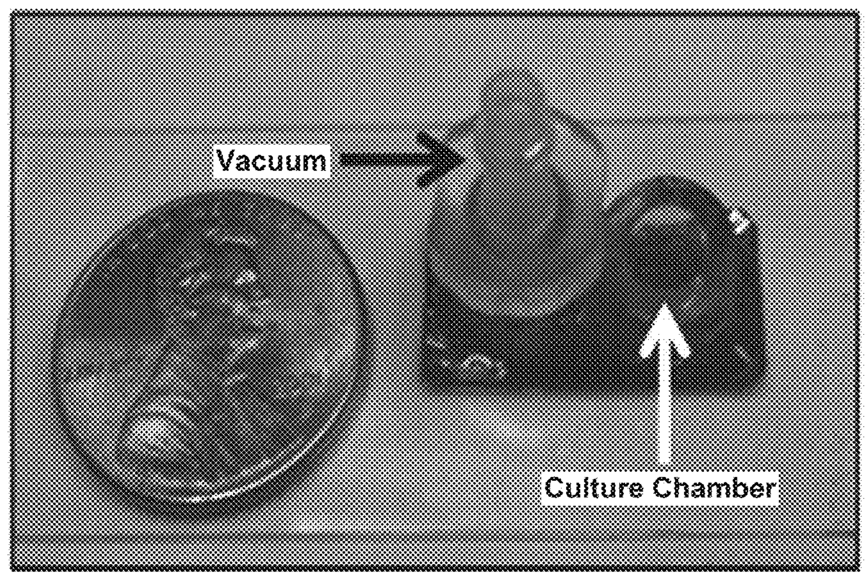
FIG. 7 is a photograph of the final device showing a culture chamber and a fitting for applying a vacuum. A penny is shown for illustrating relative size of the device as being smaller than a penny. Using this device, cells can be cultured in the culture ring and immobilized on through holes by application of negative pressure.
Figure 8:
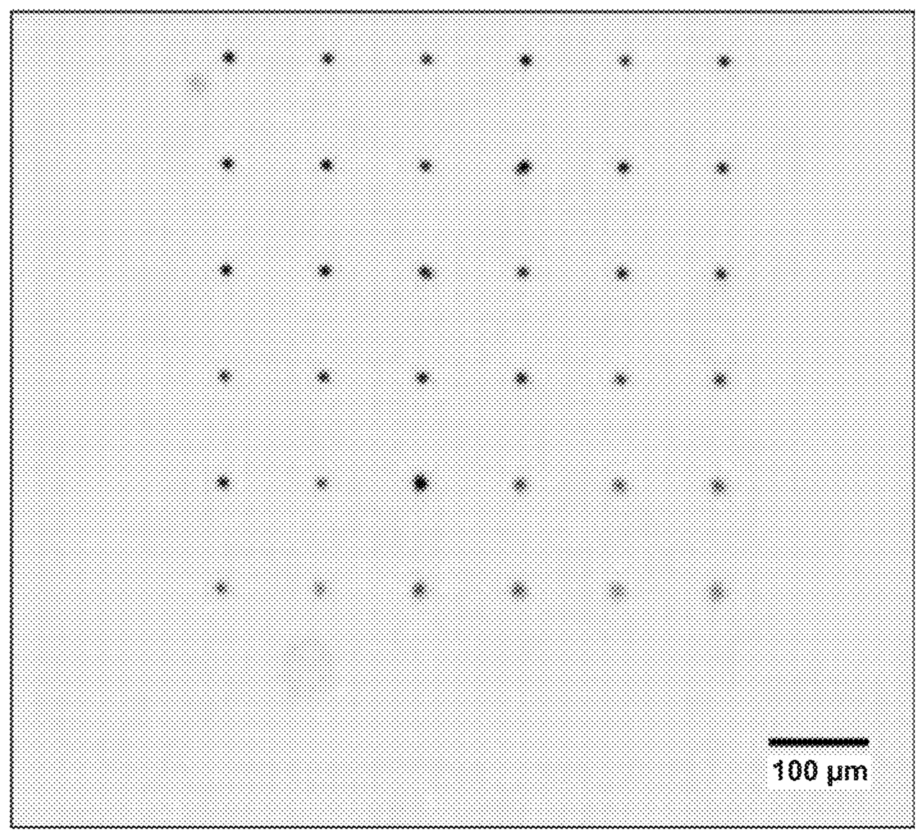
FIG. 8 is a photograph that shows a fluorescence image of 10 mm polystyrene beads immobilized on a cell sifter.

As an example, the device was tested using 10 μm fluorescent polystyrene beads (yellow green-absorption: 505; emission: 515). The beads are roughly the size of mammalian cells and provide a good model for testing the device. Beads were successfully immobilized by application of negative pressure to the device through-holes. After gentle washing it was observed that all through-holes were immobilizing a single polystyrene bead over each hole (FIG. 6E). In another example, the cell sifter was used to immobilize HeLa cells. Cells were suspended in 0.1M PBS and successfully immobilized by application of negative pressure to the through-holes.

Molecular Sensing within a Single Cell

Another aspect of the present invention is directed to the combination of a nanopipette that is functionalized to act as a sensor and coupled with an xyz controlling injection device, as shown in FIG. 1. The nanopipette sensors are geometrically extremely similar to tapered optical fiber; they can be fabricated with the same laser pulling process however the transduction mechanism is fundamentally different. Biodetection on optical fiber relies either on the detection of fluorescently tagged analyte or on an ELISA-like read out while nanopipette sensor readout is purely electrical and no biomolecule labeling is needed. The sensitivity of the nanopipette sensor is maximized at the conically shaped nanopipette tip, making the dimension and geometry of the tip orifice crucial for biosensor performance. Gating, from permanent binding at the nanoscale-sized tip opening, causes distinctive changes to the nanopipette electrical signature. The electrical changes are then detected with a simple electrochemical setup, in real time, without any need for labeling. Like optical fibers, nanopipette sensors can be integrated with piezo actuators achieving high spatial resolution as it is exploited in Scanning Ion Conductance Microscopy. This combination of nanopipette sensors and SICM is used for topographical mapping of surfaces including multiple and single cells. Another application is in detection of metabolites and molecules including proteins and nucleic acids in single living cells using label-free biosensor. In some embodiments, immunoassays can be performed inside a single living cell. Another application is in detection of oncoproteins in single cancer cells. Another application is in the measurement of bioactivity in single cells, in real time and with nanoscale resolution. For example, it can be used in studying protein-protein interactions in a single cell.

Figure 9A:
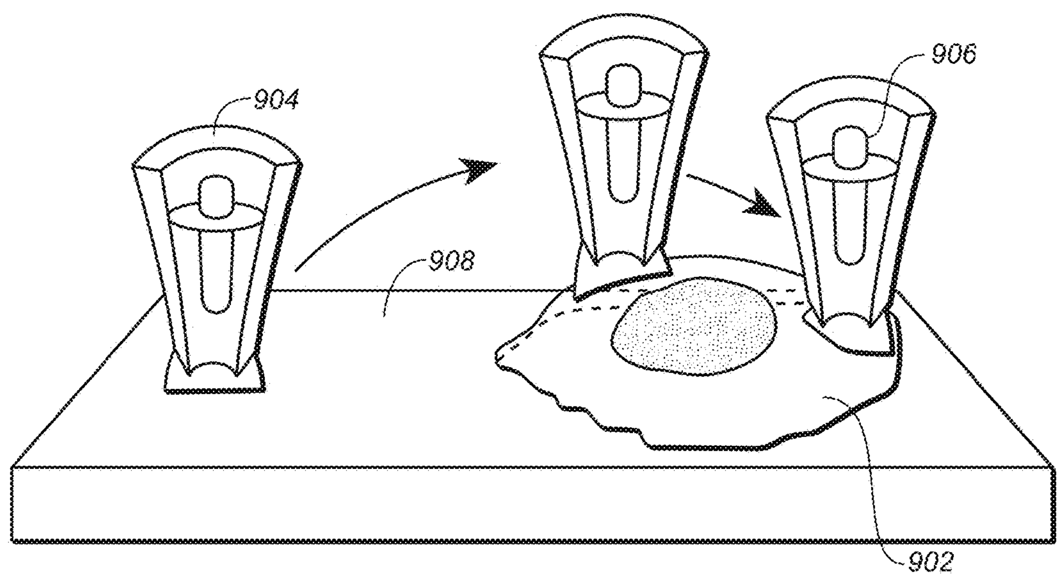
FIG. 9A is a cartoon depicting the topographical mapping with the scanning ion conductance microscopy (SICM).
Figure 9B:
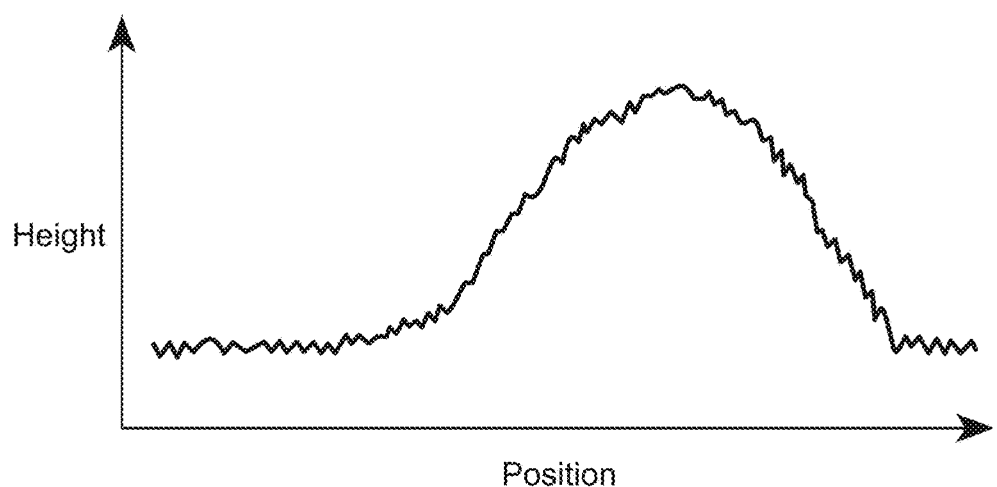
FIG. 9B is a graph of the topographical mapping, showing height of the nanopipette tip changing relative to location over a cell.

FIG. 9A is a cartoon depicting the topographical mapping of a cell using the technique embodied herein. The detection of molecules inside a cell 902 relies on a high precision nanomanipulator and a current feedback loop to insert the nanopipette sensor 904 to a defined depth into the probe cell. As a nanopipette 904 approaches the surface of a cell, the ionic current through the pipette 904, having a single bore and an electrode 906 therein, will decrease due to "current squeezing," a well known effect, exploited in scanning ion conductance microscopy. By monitoring the ionic current, the precise position of the nanopipette can be determined and controlled within ~200 nm of the cell membrane using a feedback circuit and an xyz controller as shown in FIG. 1. Additionally, the feedback mechanism ensures that the nanopipette tip does not come into contact with anything but the cell membrane, preventing the tip from potentially breaking by coming into contact with other structures or substrates. Cells may be plated on an even surface 908 (for example, a petri dish, glass slide) which is coated with a layer of a suitable polymer. Suitable polymers include organic polymers including silicon polymers e.g., silicones. An example of a silicone is polydimethylsiloxane. Cells may be covered with a suitable buffer including, but not limited to, phosphate, citrate buffers. The nanopipette sensor may be biased at a positive voltage (for example voltage between +100 mV to +1000 mV, preferably more than +500 mV) when the electroosmotic flow is directed outwards from the nanopipette barrel. This configuration avoids any cellular debris or molecules present in the medium to interact with the sensor and affect its performance. The feedback loop lowers the sensor with steps of about 10 nm until the current is reduced to 70 to 99%, preferably more than 99% of its initial value. After this initial positioning above the cell membrane the nanopipette is inserted into the cell by about 2 μm, preferably more than 1 μm, at a speed of between 50 to 200 μm/s, preferably between 80-150 μm/s. The sensor is inserted at a very high speed to reduce disturbance to the cell and maximize cell viability. Multiple penetrations can be performed on the same cell, without any noticeable change in the nanopipette current baseline and viability of the cell. Once inserted inside the cell, an AC voltage with amplitude of between 250 mV to 500 mV and frequency of between 1 to 10 Hz, preferably more than 4 Hz is applied to the nanopipette sensor to perform the sensing.

The present nanopipette sensors comprise functionalized nanopipettes, used for the sensing component of the present devices. Functionalized nanopipettes are described in an earlier US patent application publication by two of the inventors (US 2010/0072080, published Mar. 25, 2010, titled "Functionalized Nanopipette Biosensor") which is incorporated herein by reference. Briefly, nanopipettes may be functionalized by chemical linkage to molecules including polymers, polysaccharides, and biomolecules including but not limited to antibodies, peptides and biopolymers. The sensors may be coated on an interior surface with polyacrylic acid (PAA), a polymer of acrylic acid units. The formula of PAA is $(C_3H_4O_2)_n$. In a water solution at neutral pH, many of the side chains of PAA lose their protons and acquire a negative charge. This makes PAA a polyelectrolyte. The surface may be further functionalized to be bound to a polysaccharide or a protein. Detection of binding to the nanopipette sensor is based on current rectification. This refers to an effect when charged nanopores respond to a symmetric input voltage with an asymmetric current output. When the diffuse electrical double layer thickness is comparable with the pore size, the electrostatic interactions between fixed charged species on the nanopore surface and ionic species in solutions alters nanopipette permselectivity. The rectification coefficient, r, is defined as the logarithm of the ratio between the current measured at particular positive voltage and the current measured at the same voltage but with the opposed polarity.

$$r = \log_{10}\frac{I_+}{I_-}$$

This coefficient is a useful indicator of the rectifying properties of a nanopipette and therefore of the fixed charges on the sensor surface. Quartz nanopores, being negatively charged, show a negative current rectification (r<0). The rectification can be inverted (r>0) by modifying the nanopore surface with charged functional layers such as poly-L-lysine, dendrimers, aminosilane and chitosan.

EXAMPLES

Example 1: Materials and Methods

Double-barrel nanopipette fabrication: Nanopipettes were fabricated from theta quartz capillaries with an outer diameter of 1.2 mm and an inner diameter of 0.90 mm (QT120-90-7.5; Sutter Instrument Co.). The capillary was then pulled using a P-2000 laser puller (Sutter Instrument Co.) programmed with a two-line program to fabricate nanopipettes with an inner diameter of ~50 nm. Parameters used were: Heat 650, Fil 4, Vel 20, Del 170, and Pul 0; Heat 750, Fil 4, Vel 40, Del 170, and Pul 200. The resulting nanopipette tips had inner diameters ~50 nm.

Cell Culture: HeLa cells (maintained in the laboratory) were cultured (37° C., 5% $CO_2$) in Dulbecco's modified Eagle's medium (DMEM) containing 10% fetal calf serum, 1% sodium pyruvate and 1% Pen/Strep/Glu in 5% CO2 at 37° C. on a Petri dish covered with a thin layer of PDMS.

Reagents: Poly-L-lysine (PLL; 19320-A) was purchased from Electron Microscopy Sciences (Hatfield, Pa.). Dulbecco Modified Eagle's media (MT10017CV), fetal bovine serum (BW14502F), sodium pyruvate (BW13115E) and Pen/Strep/Glu (SV3008201) were purchased from Fisher. Polydimethylsiloxane was purchase from Dow Corning, (Sylgard® 184 silicon elastomer kit). (BSA, Qdots) PBS solutions at pH 7.4 were prepared using standard methods. Aqueous reagents were prepared using MilliQ water with >18MΩ$cm^{-1}$ resistance.

Measurement setup for electroosmotic ejection: The setup consisted of a low-noise amplifier (Axopatch 200B, Molecular Devices, Sunnyvale, Calif.) for pipette bias and current measurement, a micromanipulator (MP-285) for coarse control in the X, Y, and Z directions, a piezo actuator for fine control in the X, Y, and Z directions, and a FPGA (National Instruments) for hardware control of the system. The system is further modified with a low-noise high voltage source (Model 2100 Isolated Pulse Stimulator, A-M Systems), and a custom relay for switching between the low voltages required for feedback control, and the high voltages needed for electrophoretic material ejection. The system is controlled using custom coded software written in LabVIEW.

Example 2: Single Cell In Vivo Immunoassay with Nanopipette Sensors

Experimental Section

Measurement setup: Since the current flowing through the nanopipette is too small to polarize a reference electrode, a two electrode setup was used. The nanopipette sensor, acting as the working electrode, is backfilled with the working buffer, and a Ag/AgCl electrode is inserted. Another Ag/AgCl electrode is placed in bulk solution acting as auxiliary/reference electrode. Both electrodes are connected to the Axopatch 700B amplifier with the DigiData 1322A digitizer (Molecular Devices), and a PC equipped with pClamp 10 software (Molecular Devices). The system remained unstirred for the duration of the measurement, which was conducted at room temperature.

Reagents: Poly-1-lysine (PLL; 19320-A) was purchased from Electron Microscopy Sciences (Hatfield, Pa.). Polyclonal antibody HPV16 E6 (C-19) and HPV18 E6 were purchased from Santa Cruz Biotechnology, Inc. (Santa Cruz, Calif.). Dulbecco Modified Eagle's media (MT10017CV), fetal bovine serum (BW14502F), sodium pyruvate (BW13115E) and Pen/Strep/Glu (SV3008201) were purchased from Fisher. Polydimethylsiloxane was purchased from Dow Corning, (Sylgard® 184 silicon elastomer kit). PBS solutions at pH 7.4 were prepared using standard method. Aqueous reagents were prepared using MilliQ water with >18MΩ$cm^{-1}$ resistance.

Nanopipette sensor fabrication: Nanopipettes were fabricated from quartz capillaries with filaments, with an outer diameter of 1.0 mm and an inner diameter of 0.70 mm (QF100-70-5; Sutter Instrument Co.). The capillary was then pulled using a P-2000 laser puller (Sutter Instrument Co.) programmed to fabricate nanopipettes with an inner diameter of ~50 nm. Parameters used were: Heat 700, Fil 4, Vel 60, Del 150, and Pul 192. The resulting nanopipette tips had inner diameters ranging from 37 to 82 nm, with the mean diameter of 56 nm.

Antibody Immobilization: Antibodies were immobilized through the following steps. First, nanopipettes were internally coated by filling with a 0.01% solution of poly-1-lysine in water, followed by centrifugation at 4600 rpm for 3 min. The centrifugation step helps to get the solution to the very tip of the nanopipette. After the removal of excess PLL solution, the nanopipettes were baked at 120° C. for 1 h to stabilize the PLL coating. The nanopipette was then filled with a sulfo-SMCC solution (2 mg/ml, 10 mM EDTA, 50 mM PBS), centrifuged at 4600 rpm for 3 min and then incubated at room temperature for 1 h. Nanopipettes were then rinsed with 0.01M PBS and centrifugated for at least 3 times to remove any unreacted sulfo-SMCC molecules. Sulfo-SMCC contains an amine-reactive N-hydroxysuccinimide (NHS ester) that reacts with the PLL amino groups, leaving a maleimide group available for the antibodies cross link through a thioether bond. The nanopipettes were then incubated with antibody solution (10 µg/ml IgG, PBS, 1 h, 37° C.). Antibody-functionalized nanopipettes were then rinsed at least 3 times with PBS and centrifuged, to remove any unbound antibody and to provide a smooth electrolyte filling throughout the tip.

Cell lysis: Hela cells were frozen into aliquots containing ~$10^6$ cells in growing media (10% DMSO). After thawing, cells were spun down to pellet, the supernatant discarded and resuspended in 100 µL PBS solution. Covaris™, controlled by S-seried SonoLAB software, was used to lyse the cell membrane. Conditions: Duty Cycle: 5%, Intensity 3, Cycles/Burst 200, for 60 s. The cell lysate was centrifuged at 4000 rpm for 5 minutes to separate biomolecules form cell debris. The vial was placed in ice and used within 2 hours to minimize protease inhibition.

Scanning Ion Conductance Microscope: The SICM was built in-house and is based on a current amplifier (Molecular Instruments, Multiclamp 700B), a micromanipulator (Sutter Instruments, MP-285) for coarse control, and a piezo actuator (Phyzik Instrumente, NanoCube) for fine control. The setup was controlled using user customized software (LabView) developed in-house specifically for this application.

Cell Culture: HeLa cells (maintained in the laboratory) were cultured (37° C., 5% $CO_2$) in Dulbecco's modified Eagle's medium (DMEM) containing 10% fetal calf serum, 1% sodium pyruvate and 1% Pen/Strep/Glu in 5% CO2 at 37° C. on a Petri dish covered with a thin layer of PDMS.

Intracellular Protein Detection

Figure 10:
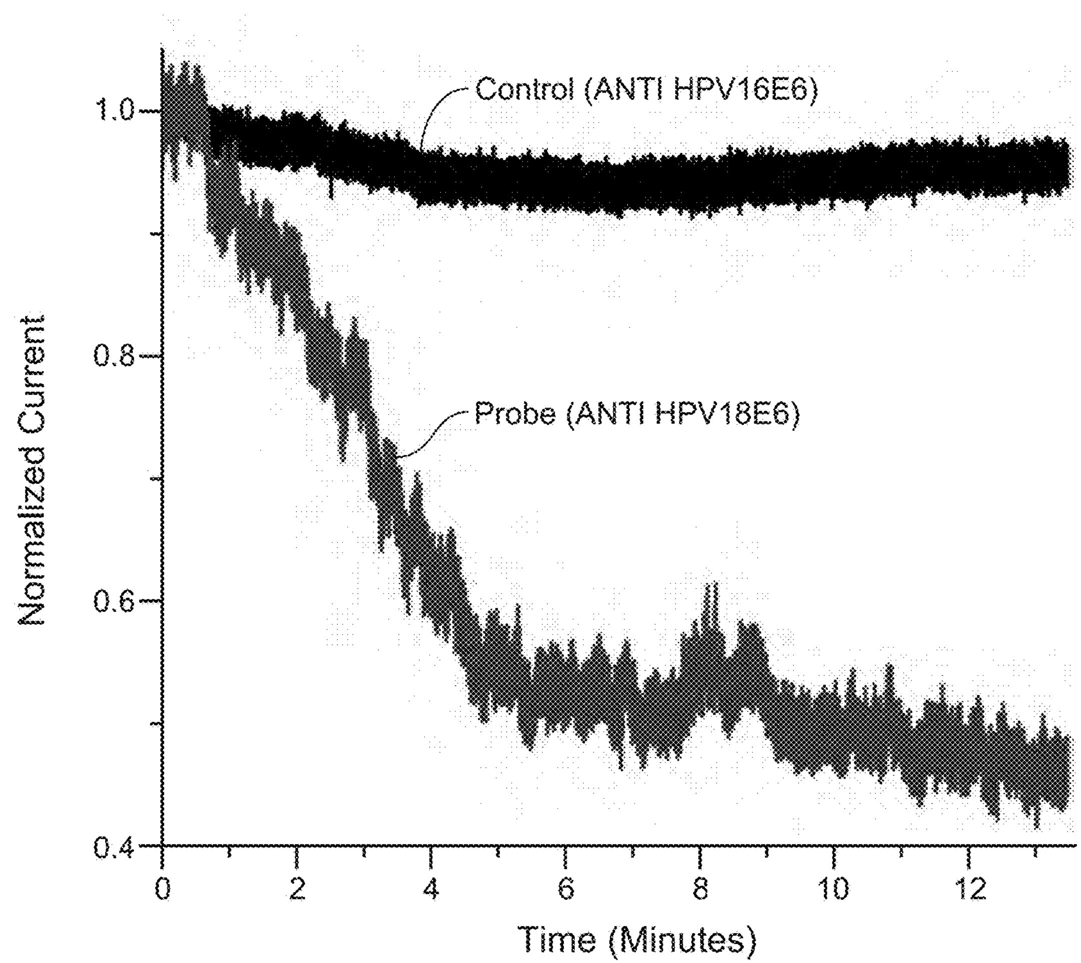
FIG. 10 is a line tracing showing selective detection of HPV18E6 antigens by nanopipette sensors. Applied Voltage:-400 mV. Antigens added at time 0.

The present nanopipette sensors can selectively detect oncoproteins in cells ex vivo. First, the selectivity of a nanopipette sensor for distinguishing different HPV genotypes was investigated. The probe sensor was functionalized with antibodies targeting HPV18E6 while the control probe contained HPV16E6. HPV-18 E6 is known to be a "malignant" protein in humans. See, Li et al., "The human papilloma virus (HPV)-18 E6 oncoprotein physically associates with Tyk2 and impairs Jak-STAT activation by interferon-alpha," Oncogene 18(42):5727-5737 (1999). HPV 16 E6 is described further at Gewin et al., "Identification of a novel telomerase repressor that interacts with the human papillomavirus type-16 E6/E6-AP complex," Genes Dev. 18(18): 2269-2282 (2004). Both sensors were immersed in a solution containing 100 pg/mL HPV18E6 antigens. The specific protein-protein interaction instantly reduced the current amplitude, through stepwise blockades, of the probe sensor (FIG. 10). Their sequential binding at the close proximity of the nanopipette sensor opening alters the local impedance, thus inducing stepwise changes in the recorded ionic current. These permanent blockades are not seen in the control sensor, whose electrical characteristic is not perturbed by the HPV18 protein E6 antigens. Furthermore, these blockades are also distinguishable from those produced by molecular translocation, as protein molecules traversing the nanopipette generate shorter and temporary blocks with a duration ranging in microseconds.

Figure 11:
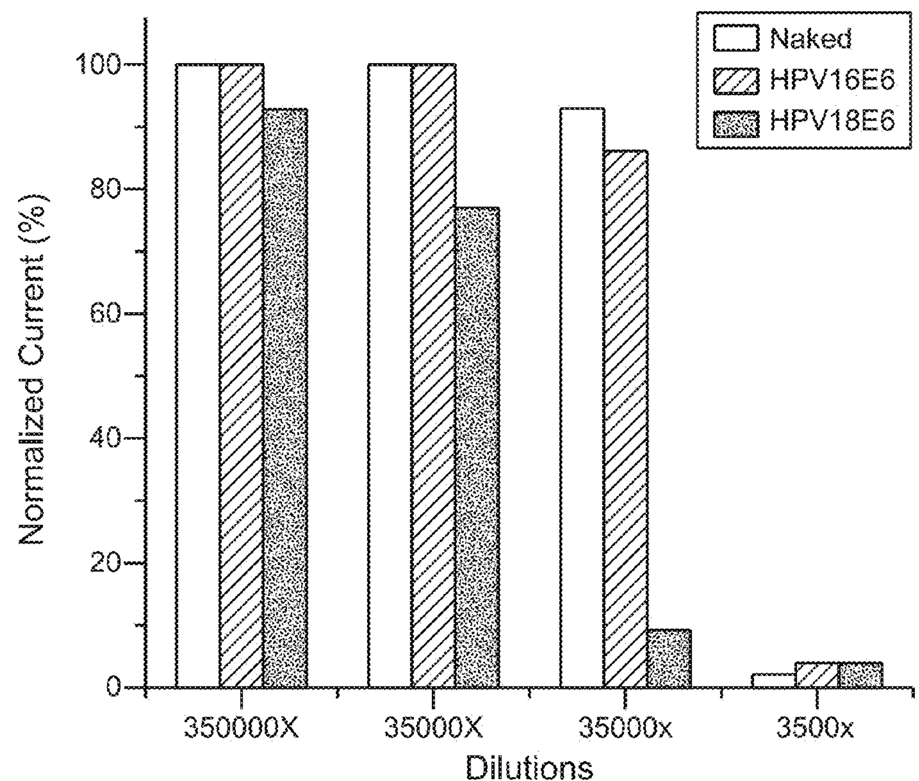
FIG. 11 is a bar graph that shows the response of nanopipette sensors to HeLa cells lysate.

Next, the selectivity of the nanopipette sensor in cell lysate was tested. Serial dilutions were performed out of aliquots containing ~$10^6$ HeLa cells to determine the sensitivity of the sensor. 350,000× dilutions does not result in any change in naked and HPV16E6 functionalized nanopipettes while a 7% change in the measured current was detected for the HPV18E6 modified nanopipette sensor (FIG. 11). Control sensors still did not respond to ten times higher concentrated samples whereas the measured current in the probe sensor dropped by 23% of its initial value. Results are summarized in Table 1.

TABLE 1

Normalized variation of the nanopipette sensor output current to serial dilution of $10^6$ HeLa cells lysate

| Dilutions | Nanopipette | HPV16E6 sensor | HPV18E6 sensor |
|---|---|---|---|
| 350000X | 100 | 100 | 93 |
| 35000X | 100 | 100 | 77 |
| 35000x | 93 | 86 | 9 |
| 3500x | 2 | 4 | 4 |

Applied voltage was shown to play a very important role to limit if not avoid non specific adsorption, however this problem should always be taken into account as it becomes predominant in concentrated solutions, as FIG. 11 shows for dilution of the cell lysate of 3500× and below where signal raised predominately form non specific adsorption. FIG. 11 also shows the percentage change on the measured current after the addition of HeLa cells lysate at different concentrations. The applied voltage was −500 mV in a PBS solution at pH 7.4.

Oncoprotein detection inside a single cell relies on a high precision nanomanipulator and a current feedback loop to insert the nanopipette sensor to a defined depth into the probe cell. As a nanopipette approaches the surface of a cell the ionic current through the pipette will decrease due to "current squeezing", a well known effect, exploited in scanning ion conductance microscopy. By monitoring the ionic current the precise position of the nanopipette can be determined and controlled within ~200 nm of the cell membrane. Additionally, the feedback mechanism ensures that the nanopipette tip does not come into contact with anything but the cell membrane, preventing the tip from potentially breaking by coming into contact with other structures or substrates. HeLa cells were plated on a Petri dish coated with layer of PDMS and covered with the complete medium.

The nanopipette sensor was biased at +500 mV when the electroosmotic flow is directed outwards from the nanopipette barrel. This configuration avoiding any cellular debris or molecules present in the medium to interact with the sensor and affect his performance. The feedback loop lowers the sensor with steps of 10 nm until the current reduced to 92% of its initial value. After this initial positioning above the cell membrane the nanopipette was inserted into the cell by 2 μm at a speed of 100 μm/s. The sensor was inserted at a very high speed to reduce disturbance to the cell and maximize cell viability. Multiple penetrations can be performed on the same cell, without any noticeable change in the nanopipette current baseline and viability of the cell. Once inserted inside the cell, an AC voltage with amplitude of 500 mV and frequency of 5 Hz was applied to the nanopipette sensor to perform the sensing.

Figure 12:
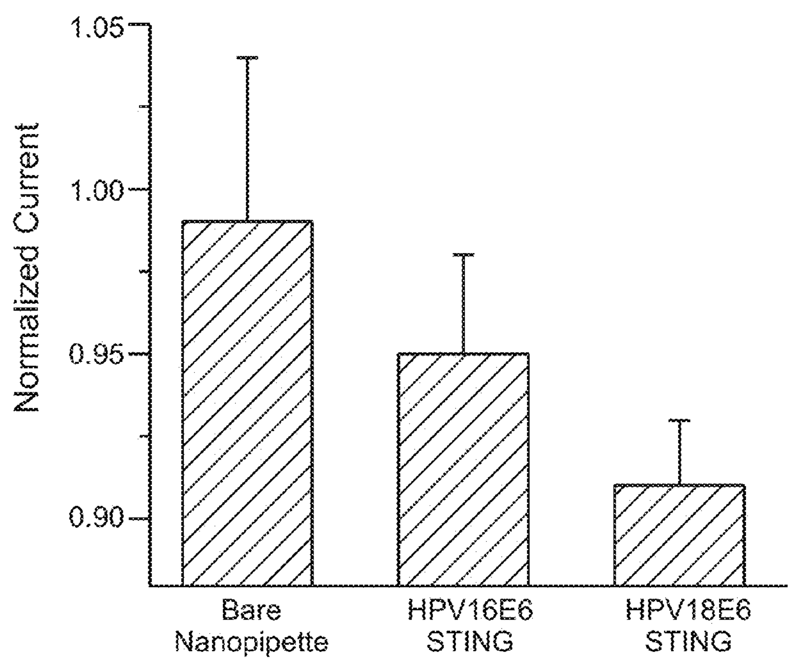
FIG. 12 is a bar graph that shows the detection of oncoproteins inside a single cell with nanopipette sensors.

FIG. 12 shows the response of nanopipette sensors inserted into HeLa cells. No noticeable change in the baseline current was detected upon insertion of a bare nanopipette into HeLa cells while a 5% decrease was measured with the control sensor functionalized with antibodies targeting HPV16E6. HeLa cells are known to be infected only with HPV 18. This was confirmed by the penetration of HeLa cells with nanopipette sensors functionalized with anti HPV18E6. An 8% current drop was measured after detection into HeLa cells due to the specific detection of HPV18E6 oncoproteins. These results indicate that nanopipette technology can allow the study of protein-protein within individual cells and without any need for labeling.

Example 3: Cell Patterning by Controlled Electroosmotic Ejection Using Quartz Nanopipettes Patterns for cells were defined using polylysine and Bovine Serum Albumin (BSA). 1 mg/ml laminin was used in the barrels of the nanopipette and deposited directly onto a PDMS substrate in a 35 mm Petri dish. Pattern deposition was confirmed by mixing quantum dots with the electrolyte solution. Patterns could then be assessed using fluorescence microscopy to visualize deposition, and check for errors in printing. The substrate was then washed with lmg/ml BSA in a self masking step. After pattern definition the substrate was immersed in cell culture media. HeLa cells were used as model cells in these studies for their ease of use and robustness. Cells were dispersed in media and allowed to settle onto the substrate. After several hours of incubation cells were gently rinsed with pre-warmed culture media to remove any cells not firmly attached to the substrate. Cell attachment was assessed both qualitatively and quantitatively.

Conclusion

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method of detecting an analyte in a single living cell, comprising:

positioning a tip of a nanopipette within 50 to 200 nm of the cell membrane of the living cell, wherein the nanopipette comprises a working electrode disposed in the nanopipette in contact with a solution in the nanopipette, wherein the nanopipette is functionalized with an analyte-binding reagent, wherein the nanopipette is biased at a positive voltage by a circuit connected to the working electrode and to a reference electrode positioned in a liquid contacting the single living cell;

inserting the tip of the nanopipette to a defined depth into the single living cell, wherein the positioning and inserting is controlled via an xyz controller monitoring current through the tip of the nanopipette;

detecting the analyte in the single living cell by detecting a reduction in current through the tip of the nanopipette.

2. The method according to claim 1, wherein the inserting is at a speed of from 50 to 200 μm/s.

3. The method according to claim 2, wherein the inserting is at a speed of 80 to 150 μm/s.

4. The method according to claim 1, wherein the analyte-binding reagent is immobilized on an interior surface of the nanopipette at or near the tip of the nanopipette.

5. The method according to claim 4, wherein the analyte-binding reagent is linked by sulfo-succinimidyl-4-(N-maleimidomethyl)cyclohexane-1-carboxylate (sulfo-SMCC) to a poly-1-lysine (PLL) coating on the interior surface.

6. The method according to claim 1, wherein the tip of the nanopipette has a diameter of from 37 to 82 nm.

7. The method according to claim 1, wherein the analyte-binding reagent is an antibody specific for the analyte.

8. The method according to claim 1, wherein the analyte-binding reagent is an aptamer specific for the analyte.

9. The method according to claim 1, wherein the analyte is a receptor and the analyte-binding reagent is a ligand of the receptor.

10. The method according to claim 1, wherein the analyte is a ligand and the analyte-binding reagent is a receptor of the ligand.

11. The method according to claim 1, wherein the analyte is an oncoprotein.

12. The method according to claim 1, further comprising, prior to the inserting, immobilizing the single living cell on a substrate.

13. The method according to claim 12, wherein immobilizing the single living cell on the substrate comprises placing the cell in a cavity in the substrate, the cavity sized to hold only a single cell.

14. The method according to claim 12, comprising applying a pressure differential across the cavity to aid in immobilizing the single living cell.

15. The method according to claim 13, wherein the substrate comprises one or more through-holes for applying negative pressure to immobilize the single living cell in the cavity.

16. The method according to claim 1, wherein the single living cell is a bacterial cell or a fungal cell.

17. The method according to claim 1, wherein the single living cell is an animal cell.

18. The method according to claim 17, wherein the animal cell is a mammalian cell.

19. The method according to claim 18, wherein the mammalian cell is a HeLa cell.

20. The method according to claim 1, wherein the predefined depth is between 1 μm to 2 μm.

* * * * *